United States Patent
Chow et al.

(10) Patent No.: US 8,183,393 B2
(45) Date of Patent: May 22, 2012

(54) DYE COMPOUND AND DYE-SENSITIZED SOLAR CELL

(75) Inventors: Tahsin J. Chow, Taipei County (TW); Yuan-Chieh Chang, Taichung (TW)

(73) Assignee: Academia Sinica, Taipei (TW)

( * ) Notice: Subject to any disclaimer, the term of this patent is extended or adjusted under 35 U.S.C. 154(b) by 368 days.

(21) Appl. No.: 12/468,069

(22) Filed: May 19, 2009

(65) Prior Publication Data

US 2010/0076205 A1    Mar. 25, 2010

(30) Foreign Application Priority Data

Sep. 25, 2008    (TW) ............................... 97136805 A

(51) Int. Cl.
*C07D 333/10*    (2006.01)

(52) U.S. Cl. ............................... 549/77; 549/29; 549/74

(58) Field of Classification Search .................. 558/303, 558/388, 410; 549/29, 59, 74, 77
See application file for complete search history.

(56) References Cited

OTHER PUBLICATIONS

Yen et al (2008): STN International HCAPLUS database, (Columbus, Ohio), Accession number: 2008:856600.*
Ando et al (2004): STN International HCAPLUS database, (Columbus, Ohio), Accession number: 2004:873947.*
Inoue et al (2007): STN International HCAPLUS database, (Columbus, Ohio), Accession number: 2007:61646.*
Yen et al (2008): J. Phys. Chem, vol. 112, pp. 12557-12567.*

\* cited by examiner

*Primary Examiner* — Golam M M Shameem
(74) *Attorney, Agent, or Firm* — Jianq Chyun IP Office

(57) ABSTRACT

A dye compound is described, which is expressed by formula (I):

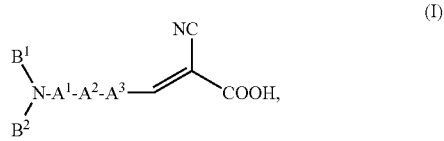

wherein $A^1$, $A^2$ and $A^3$ each independently represent a substituted or unsubstituted 1,4-phenylene or 2,5-thiophene group, and $B^1$ and $B^2$ each independently represent a substituted or unsubstituted aryl group. The dye compound is suitably used as a dye sensitizer in a dye sensitized solar cell (DSSC).

7 Claims, 6 Drawing Sheets

DYE COMPOUND AND DYE-SENSITIZED SOLAR CELL

CROSS-REFERENCE TO RELATED APPLICATION

This application claims the priority benefit of Taiwan application serial no. 97136805, filed on Sep. 25, 2008. The entirety of the above-mentioned patent application is hereby incorporated by reference herein and made a part of specification.

BACKGROUND OF THE INVENTION

1. Field of the Invention

This invention relates to dye compounds, and more particularly relates to a dye compound that can be used as a dye sensitizer in a dye-sensitized solar cell (DSSC), and to a DSSC using the dye compound as a dye sensitizer.

2. Description of the Related Art

The demand for carbon reduction has triggered the search for renewable energy sources, such as solar cells. Although Si-based semiconductors dominated solar cell applications for decades, recent development of DSSCs proves application of organic and organometallic dyes in this field. The DSSC is promising to be commercialized in the future, mainly because of its low cost, simple fabrication and high flexibility.

A DSSC can be formed by coating a porous film of nanocrystalline $TiO_2$ on a conductive glass piece, adsorbing a dye on $TiO_2$ and combining the resulting structure with a redox electrolytic solution and another conductive glass piece having a metal electrode thereon. When the dye molecule is excited by light, charge separation is induced therein, and an electric current is caused due to subsequent charge transfer to the electrolyte and $TiO_2$.

When a ruthenium-based dye like N719 is used, the DSSC can have a conversion efficiency up to 11% at most. However, since such Ru-based dyes are very expensive, the study has turned to the application of non-metal dyes in DSSCs.

SUMMARY OF THE INVENTION

In view of the foregoing, this invention provides a dye compound, which can be used as a dye sensitizer in a DSSC.

This invention also provides a DSSC using the dye compound of this invention.

The dye compound of this invention is expressed by formula (I):

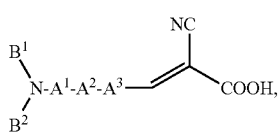

(I)

wherein $A^1$, $A^2$ and $A^3$ each independently represent a substituted or unsubstituted 1,4-phenylene or 2,5-thiophene group, and $B^1$ and $B^2$ each independently represent a substituted or unsubstituted aryl group. The dye compound can be applied to a DSSC.

In certain embodiments, the above groups $B^1$ and $B^2$ are each independently a phenyl group or a naphthyl group, in which arbitrary hydrogen atom can be substituted by a $C_1$-$C_3$ alkyl group or a $C_1$-$C_3$ alkoxy group.

It is to be understood that both the foregoing general description and the following detailed description are exemplary, and are intended to provide further explanation of the invention as claimed.

DESCRIPTION OF EMBODIMENTS

Figure 1:
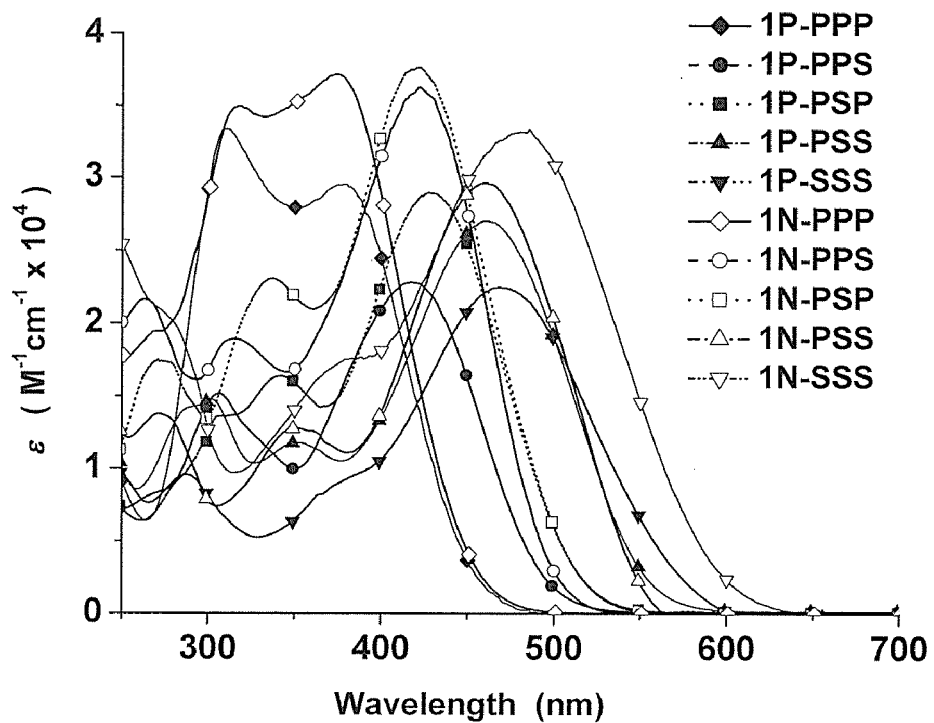
FIG. 1 shows the absorption spectra (in THF) of the dye compounds obtained in Example 1 of this invention, where "ε" is the molar extinction coefficient.

The dye compound of this invention, which is suitably used as a dye sensitizer in a DSSC, is expressed by formula (I):

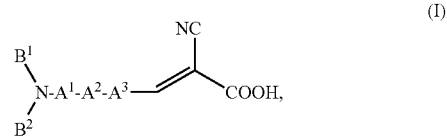

(I)

wherein $A^1$, $A^2$ and $A^3$ each independently represent a substituted or unsubstituted 1,4-phenylene or 2,5-thiophene group, and $B^1$ and $B^2$ each independently represent a substituted or unsubstituted aryl group.

In an embodiment, the above groups $B^1$ and $B^2$ each independently represent a phenyl group or a naphthyl group, in which arbitrary hydrogen atom can be substituted by a $C_1$-$C_3$ alkyl group or a $C_1$-$C_3$ alkoxy group.

EXAMPLES

Example 1

Among the compounds in which $B^1$ and $B^2$ each independently represent phenyl or naphthyl, the following compounds were synthesized, measured for their properties and tested for their light-harvesting performances as dye sensitizers in DSSCs.

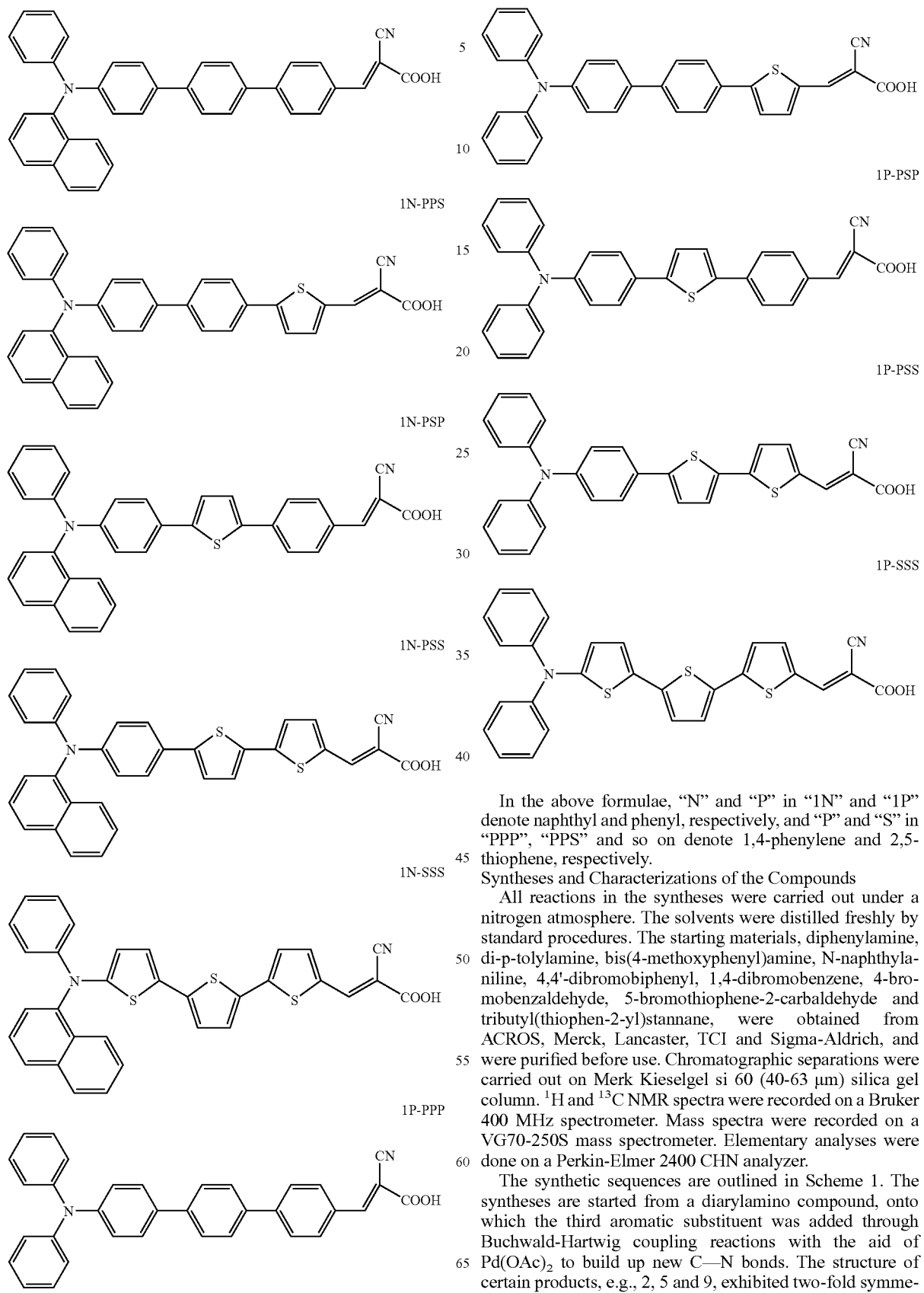

In the above formulae, "N" and "P" in "1N" and "1P" denote naphthyl and phenyl, respectively, and "P" and "S" in "PPP", "PPS" and so on denote 1,4-phenylene and 2,5-thiophene, respectively.

Syntheses and Characterizations of the Compounds

All reactions in the syntheses were carried out under a nitrogen atmosphere. The solvents were distilled freshly by standard procedures. The starting materials, diphenylamine, di-p-tolylamine, bis(4-methoxyphenyl)amine, N-naphthyla- niline, 4,4'-dibromobiphenyl, 1,4-dibromobenzene, 4-bro- mobenzaldehyde, 5-bromothiophene-2-carbaldehyde and tributyl(thiophen-2-yl)stannane, were obtained from ACROS, Merck, Lancaster, TCI and Sigma-Aldrich, and were purified before use. Chromatographic separations were carried out on Merk Kieselgel si 60 (40-63 µm) silica gel column. $^1$H and $^{13}$C NMR spectra were recorded on a Bruker 400 MHz spectrometer. Mass spectra were recorded on a VG70-250S mass spectrometer. Elementary analyses were done on a Perkin-Elmer 2400 CHN analyzer.

The synthetic sequences are outlined in Scheme 1. The syntheses are started from a diarylamino compound, onto which the third aromatic substituent was added through Buchwald-Hartwig coupling reactions with the aid of Pd(OAc)$_2$ to build up new C—N bonds. The structure of certain products, e.g., 2, 5 and 9, exhibited two-fold symme- try, which can be justified by their $^1$H and $^{13}$C NMR spectra.

Scheme 1
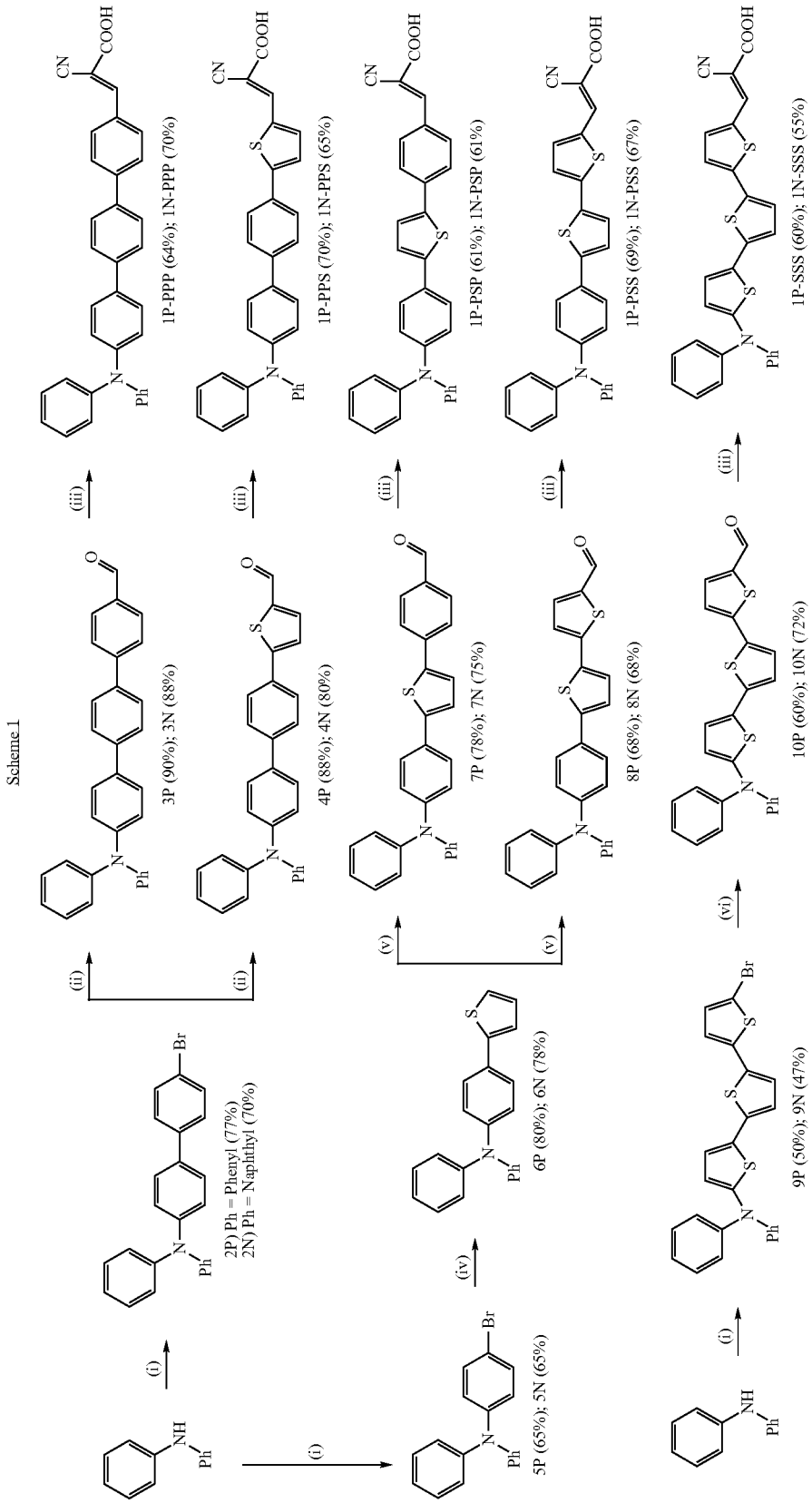

It is particularly noted that the trithiophenylene linkage in compounds 9P and 9N was completed in a single step, and a subsequent formylation was done by Vilsmeier-Haack reaction to give 10P and 10N. For compounds 2P and 2N, extension of the aryl chain was achieved by Suzuki coupling reactions to yield the aldehydes 3P, 3N, 4P and 4N in 80-90% yields. The addition of a thiophene unit on 5P and 5N was done by Stille coupling with 2-bromothiophene to give 6P and 6N in about 80% yield. A similar type of reaction was performed again to put on the third aryl groups in 7P-8N in 68-78% yields. The final step was a Knoevenagel condensation with cyanoacetic acid to convert carbaldehydes to cyanoacrylic acids. All final products can be crystallized into deep color solids. All reactions in Scheme 1 are described below in more details.

Synthesis of
4-bromo-4'-(naphthylphenylamino)biphenyl (2N)

A mixture of 4,4'-dibromobiphenyl (8.46 g=27.4 mmol), $Pd(OAc)_2$ (105 mg=0.18 mmol), dppf (253 mg=0.46 mmol), N-(1-naphthyl)aniline (2.0 g=9.13 mmol) and sodium t-butoxide (1.32 g=13.7 mmol) in dry toluene was placed in a three-necked flask under a nitrogen atmosphere and stirred at 90° C. for 15 h. After cooling, the reaction was quenched by adding water and then extracted by ethyl acetate. The organic layer was dried over anhydrous $MgSO_4$ and evaporated under vacuum. The products were purified by a silica gel column eluted with hexane. White solid of compound 2N was obtained in 70% yield (2.86 g=6.37 mmol).

The spectroscopic data of compound 2N were as follows: $^1H$ NMR ($CDCl_3$): δ 7.95 (d, 1H, J=7.9 Hz), 7.90 (d, 1H, J=7.9 Hz), 7.79 (d, 1H, J=8.2 Hz), 7.44-7.52 (m, 4H), 7.35-7.41 (m, 6H), 7.20-7.24 (m, 2H), 7.03-7.11 (m, 4H) and 6.97 (t, 1H, J=7.3 Hz); $^{13}C$ NMR ($CDCl_3$): δ 148.1, 147.9, 143.1, 139.5, 135.2, 132.5, 131.7, 131.2, 129.1, 128.4, 128.0, 127.4, 127.2, 126.6, 126.4, 126.3, 126.1, 124.1, 122.3, 122.1, 121.3 and 120.6; HRMS (m/z): 449.0783 ($M^+$) (calculated value: 449.0779).

Synthesis of 4-bromo-4'-diphenylaminobiphenyl (2P)

Compound 2P was synthesized in a procedure similar to that for 2N except that N-(1-naphthyl)aniline was replaced by N-phenylaniline in the same mole number, giving compound 2P as yellow solid in 80% yield.

The spectroscopic data of compound 2P were as follows: $^1H$ NMR ($CDCl_3$): δ 7.52 (d, 2H, J=8.6 Hz), 7.42 (dd, 4H, J=8.7, 1.3 Hz), 7.26 (dd, 4H, J=6.8, 1.8 Hz), 7.12 (dt, 6H, J=8.7, 1.8 Hz) and 7.02 (d, 2H, J=7.3 Hz); $^{13}C$ NMR ($CDCl_3$): δ 147.5, 139.5, 133.5, 131.7, 129.3, 129.2, 128.1, 127.4, 124.5, 124.3, 123.6, 123.0 and 120.8; HRMS (m/z): 399.0633 ($M^+$) (calculated value: 339.0623).

Synthesis of 4'-(naphthylphenylamino)triphenylene-4-carbaldehyde (3N)

To a three-necked round-bottom flask containing 2N (6.82 g=15.2 mmol) was added dropwise BuLi (16.1 mmol, 1.6 M in a hexane solution of 10 mL) in dry THF at −78° C., and then the solution was brought to 0° C. and stirred by a magnetic bar for 30 minutes. The solution was cooled again to −78° C. and to it was added dropwise tri-isopropyl borate (5.3 mL=19.8 mmol). The reaction solution was warmed up gradually to room temperature and stirred overnight. To the reaction solution was then added excess amount (30 mL) of 10% $HCl_{(aq)}$, while the mixture was stirred for another 1 hour. The reaction was quenched by pouring into distilled water, followed by extraction with ethyl acetate. The organic layer was dried over anhydrous $MgSO_4$, and evaporation of the solvent gave a crude product, which was immediately subjected to the next reaction.

The crude product was mixed with 4-bromobenzaldehyde (2.57 g=14.0 mmol), $K_2CO_{3(aq)}$ (2.76 g=2 mmol) in 10 mL of $H_2O$, and $Pd(PPh_3)_4$ (807 mg=0.69 mmol) in dry toluene/THF (2/1). The mixture was heated to 90° C. for 12 hours. After cooling, the products were extracted by ethyl acetate and the organic layer dried over anhydrous $MgSO_4$. The crude product was dried in vacuo and purifies by a silica gel column eluted with $CH_2Cl_2$/hexane (1/1). Yellow solid of compound 3N was obtained in 88% yield (6.35 g=13.4 mmol).

The spectroscopic data of 3N were as follows: $^1H$ NMR ($CDCl_3$): δ 10.04 (s, 1H), 7.93-7.95 (m, 3H), 7.88 (d, 1H, J=8.1 Hz), 7.78 (t, 3H, J=6.9 Hz), 7.67 (d, 2H, J=8.6 Hz), 7.64 (d, 2H, J=8.6 Hz), 7.44-7.50 (m, 4H), 7.35-7.38 (m, 2H), 7.24 (d, 1H, J=4.2 Hz), 7.21 (d, 2H, J=7.2 Hz), 7.10 (d, 2H, J=8.6 Hz), 7.07 (d, 2H, J=8.6 Hz) and 6.96 (t, 1H, J=7.2 Hz); $^{13}C$ NMR ($CDCl_3$): δ 191.7, 148.2, 148.0, 146.6, 143.3, 140.8, 137.6, 135.3, 135.1, 132.8, 131.3, 130.3, 129.2, 128.5, 127.7, 127.6, 127.3, 127.0, 126.7, 126.4, 124.5, 124.2, 122.4, 122.3 and 121.5; HRMS (m/z): 475.1933 ($M^+$) (calculated value: 475.1936).

Synthesis of 4'-(diphenylamino)triphenylene-4-carbaldehyde (3P)

Compound 3P was synthesized in a procedure similar to that for 3N except that compound 2N was replaced by 2P in the same mole number, giving compound 3P as yellow solid in 90% yield.

The spectroscopic data of 3P were as follows: $^1H$ NMR ($CDCl_3$): δ 10.62 (s, 1H), 7.96 (d, 2H, J=8.2 Hz), 7.80 (d, 2H, J=8.2 Hz), 7.67-7.72 (m, 4H), 7.52 (d, 2H, J=8.6 Hz), 7.25-7.31 (m, 5H), 7.14-7.17 (m, 5H) and 7.02 (t, 2H, J=7.3 Hz); $^{13}C$ NMR ($CDCl_3$): δ 191.8, 147.6, 147.5, 146.6, 140.7, 137.8, 135.0, 133.8, 130.2, 129.2, 127.6, 127.3, 127.0, 124.5, 123.6 and 123.0; HRMS (m/z): 426.1859 ($M^+$) (calculated value: 426.1858).

Synthesis of 5-(naphthylphenylamino)biphenylenethiophene-2-carbaldehyde (4N)

Compound 4N was synthesized in a procedure similar to that for 3N except that 4-bromobenzaldehyde was replaced by 5-bromothiophene-2-carbaldehyde in the same mole number, giving compound 4N as yellow solid in 80% yield.

The spectroscopic data of 4N were as follows: $^1H$ NMR ($CDCl_3$): δ 9.88 (s, 1H), 7.98 (d, 1H, J=8.4 Hz), 7.91 (d, 1H, J=8.2 Hz), 7.81 (d, 1H, J=8.2 Hz), 7.71 (d, 1H, J=4.0 Hz), 7.69 (d, 2H, J=8.4 Hz), 7.59 (d, 2H, J=8.4 Hz), 7.36-7.52 (m, 7H), 7.22-7.26 (m, 2H), 7.13 (d, 2H, J=7.6 Hz), 7.07 (d, 2H, J=8.6 Hz) and 7.00 (t, 1H, J=7.3 Hz); $^{13}C$ NMR ($CDCl_3$): δ 182.6, 154.1, 148.3, 147.9, 143.1, 142.1, 141.6, 137.4, 135.3, 132.3, 131.2, 131.1, 129.2, 128.4, 127.4, 127.3, 126.9, 126.7, 126.5, 126.3, 126.2, 124.1, 123.7, 122.5, 122.3 and 121.2; HRMS (m/z): 481.1505 ($M^+$) (calculated value: 481.1500).

Synthesis of 5-(diphenylaminobiphenylene) thiophene-2-carbaldehyde (4P)

Compound 4P was synthesized in a procedure similar to that for 4N except that compound 2N was replaced by 2P in the same mole number, giving yellow solid of compound 4P in 88% yield.

The spectroscopic data of 4P were as follows: $^1$H NMR (CDCl$_3$): δ 9.89 (s, 1H), 7.74 (d, 1H, J=3.9 Hz), 7.72 (d, 2H, J=8.4 Hz), 7.63 (d, 2H, J=8.4 Hz), 7.50 (d, 2H, J=8.6 Hz), 7.42 (d, 1H, J=3.9 Hz), 7.25-7.30 (m, 4H), 7.13-7.15 (m, 6H) and 7.05 (t, 2H, J=7.3 Hz); $^{13}$C NMR (CDCl$_3$): δ 182.0, 154.0, 147.7, 147.4, 142.1, 141.6, 137.4, 133.3, 131.3, 129.3, 127.5, 127.1, 126.7, 124.6, 123.8, 123.4 and 123.1; HRMS (m/z): 431.1349 (M$^+$) (calculated value: 431.1344).

Synthesis of p-bromo-N-naphthyl-N-phenylaniline (5N)

Compound 5N was synthesized in a procedure similar to that for 2N except that 4,4'-dibromobiphenyl was replaced by 1,4-dibromobenzene in the same mole number, giving compound 5N as white solid in 65% yield.

The spectroscopic data of 5N were as follows: $^1$H NMR (CDCl$_3$): δ 7.86 (d, 2H, J=9.17 Hz), 7.76 (d, 1H, J=8.1 Hz), 7.45 (t, 2H, J=7.8 Hz), 7.34 (t, 1H, J=7.8 Hz), 7.28 (d, 1H, J=7.3 Hz), 7.16-7.25 (m, 4H), 7.02 (d, 2H, J=7.7 Hz), 6.94 (t, 1H, J=7.3 Hz) and 6.84 (dt, 2H, J=8.9, 2.6 Hz); $^{13}$C NMR (CDCl$_3$): δ 147.8, 147.5, 142.9, 135.2, 131.9, 130.9, 129.2, 128.4, 127.1, 126.7, 126.5, 126.3, 126.2, 123.9, 122.7, 122.3, 122.1 and 113.5; HRMS (m/z): 373.0475 (M$^+$) (calculated value: 373.0466).

Synthesis of p-bromo-N,N-diphenylaniline (5P)

Compound 5P was synthesized in a procedure similar to that for 5N except that N-(1-naphthyl)aniline was replaced by N-phenylaniline in the same mole number, giving compound 5P as white solid in 65% yield.

The spectroscopic data of 5P were as follows: $^1$H NMR (CDCl$_3$): δ 7.32 (t, 2H, J=8.8 Hz), 7.20-7.29 (m, 4H), 7.05 (t, 4H, J=7.3 Hz), 6.96-7.02 (m, 2H) and 6.90-6.93 (m, 2H); $^{13}$C NMR (CDCl$_3$): δ 147.3, 146.9, 132.1, 129.3, 125.0, 124.3, 123.1 and 114.7; HRMS (m/z): 323.0309 (M$^+$) (calculated value: 323.0310).

Synthesis of N-naphthyl-N-phenyl-p-(2'-thiophenyl) aniline (6N)

To a three-necked flask containing a mixture of 5N (2.3 g=6.19 mmol), PdCl$_2$(PPh$_3$)$_2$ (0.13 g=0.18 mmol) and 2-tributylstannylthiophene (5.3 mL=14.2 mmol) was added DMF (20 mL). The reaction mixture was stirred at 90° C. for 24 hours. After cooling, the reaction was quenched by adding MeOH and KF$_{(aq)}$ (saturated 15 mL). The mixture was extracted by CH$_2$Cl$_2$ and the organic layer dried by anhydrous MgSO$_4$. Evaporation of the solvent gave a crude product, which was purified by silica gel with hexane as eluent to obtain the product as white solid in 78% yield (1.82 g=4.82 mmol).

The spectroscopic data of 6N were as follows: $^1$H NMR (CDCl$_3$): δ 7.93 (d, 1H, J=8.2 Hz), 7.88 (d, 1H, J=8.2 Hz), 7.78 (d, 1H, J=8.2 Hz), 7.33-7.49 (m, 6H), 7.17-7.23 (m, 4H) and 6.94-7.08 (m, 6H); $^{13}$C NMR (CDCl$_3$): δ 148.0, 147.8, 144.3, 143.1, 135.2, 131.1, 129.1, 128.3, 127.8, 127.1, 126.6, 126.5, 126.4, 126.3, 124.1, 123.7, 122.2, 122.0, 121.9 & 121.4; HRMS (m/z): 377.1212 (M$^+$) (calculated value: 377.1204).

Synthesis of N,N-diphenyl-p-(2'-thiophenyl)aniline (6P)

Compound 6P was synthesized in a procedure similar to that for 6N except that compound 5N was replaced by 5P in the same mole number, giving compound 6P as white solid in 80%.

The spectroscopic data of 6P were as follows: $^1$H NMR (CDCl$_3$): δ 7.46 (d, 2H, J=8.6 Hz), 7.25 (d, 2H, J=7.5 Hz), 7.24 (d, 2H, J=7.4 Hz), 7.19-7.21 (m, 2H), 7.10 (d, 4H, J=7.5 Hz), 7.05 (d, 2H, J=8.4 Hz) and 7.00-7.03 (m, 3H); $^{13}$C NMR (CDCl$_3$): δ 147.4, 147.1, 144.2, 129.2, 128.5, 127.9, 126.6, 124.4, 123.9, 123.7, 122.9 and 122.1; HRMS (m/z): 327.1084 (M$^+$) (calculated value: 327.1082).

Synthesis of p-(5-(p-(naphthylphenylamino)phenyl) thiophen-2-yl)benzaldehyde(7N)

To a three-necked flask containing a mixture of 6N (4.67 g=12.4 mmol) in dry THF was adding dropwise BuLi (16.1 mmol, 1.6 M in a hexane solution of 10 mL) at −78° C., then the solution was allowed to warm up gradually to 0° C. for about 30 minutes. The solution was cooled again to −78° C., and to it was added dropwise tri-n-butylchloro-stannane (5.3 mL=16.1 mmol). The reaction solution was then warmed up to room temperature and stirred overnight. The reaction was quenched by adding water and extracted by CH$_2$Cl$_2$. The combined organic solution was dried by anhydrous MgSO$_4$ and then dried in vacuo to produce a crude product.

The crude product was dissolved in dry DMF, to which were added p-bromo-benzaldehyde (2.28 g=12.38 mmol) and PdCl$_2$(PPh$_3$)$_2$ (237 mg=0.37 mmol). The solution was heated to 90° C. for 24 hours and then cooled. The reaction was quenched by adding MeOH and KF$_{(aq)}$ (saturated 15 mL). The mixture was extracted by CH$_2$Cl$_2$, while the organic layer was dried over anhydrous MgSO$_4$. Evaporation of the solvent gave a product, which was purified by a silica gel column eluted with CH$_2$Cl$_2$/hexane (1/1) to obtain compound 7N as white solid in 75% yield (4.47 g=9.3 mmol).

The spectroscopic data of 7N were as follows: $^1$H NMR (CDCl$_3$): δ 9.97 (s, 1H), 7.91 (d, 1H, J=8.6 Hz), 7.88 (d, 1H, J=7.8 Hz), 7.84 (d, 2H, J=8.4 Hz), 7.78 (d, 1H, J=8.2 Hz), 7.72 (d, 2H, J=8.2 Hz), 7.34-7.49 (m, 7H) and 6.96-7.23 (m, 8H); $^{13}$C NMR (CDCl$_3$): δ 191.3, 148.4, 147.7, 146.1, 142.9, 140.3, 140.1, 135.2, 134.7, 131.1, 130.4, 129.2, 128.4, 127.3, 126.8, 126.6, 126.5, 126.4, 126.3, 126.2, 126.0, 125.4, 124.0, 123.1, 122.6, 122.5 and 121.0; HRMS (m/z): 481.1498 (M$^+$) (calculated value: 481.1500).

Synthesis of p-(5-(p-(diphenylamino)phenyl) thiophen-2-yl)-benzaldehyde (7P)

Compound 7P was synthesized in a procedure similar to that for 7N except that compound 6N was replaced by 6P in the same mole ratio, giving compound 7P as white solid in 78% yield.

The spectroscopic data of 7P were as follows: $^1$H NMR (CDCl$_3$): δ 10.00 (s, 1H), 7.89 (d, 2H, J=8.5 Hz), 7.76 (d, 2H, J=8.3 Hz), 7.51 (d, 2H, J=8.7 Hz), 7.43 (d, 1H, J=3.8 Hz), 7.27-7.31 (m, 4H), 7.24 (d, 1H, J=3.8 Hz) and 7.05-7.10 (m, 8H); $^{13}$C NMR (CDCl$_3$): δ 191.3, 147.8, 147.2, 145.9, 140.61, 140.1, 134.8, 130.4, 129.3, 127.5, 126.5, 126.0, 125.4, 124.6, 123.4, 123.3 and 123.2; HRMS (m/z): 431.1342 (M$^+$) (calculated value: 431.1344).

Synthesis of 5-(5'-(p-(naphthylphenylamino)phenyl) thiophen-2'-yl)thiophene-2-carbaldehyde (8N)

Compound 8N was synthesized in a procedure similar to that for 7N except that 4-bromobenzaldehyde was replaced by 5-bromothiophene-2-carbaldehyde in the same mole number, giving compound 8N as orange solid in 68% yield.

The spectroscopic data of 8N were as follows: $^1$H NMR (CDCl$_3$): δ 9.82 (s, 1H), 7.97 (d, 1H, J=8.4 Hz), 7.92 (d, 1H, J=8.2 Hz), 7.82 (d, 1H, J=8.2 Hz), 7.57 (d, 1H, J=4.0 Hz), 7.46-7.51 (m, 4H), 7.36-7.40 (m, 4H), 7.26 (d, 1H, J=4.0 Hz), 7.24 (d, 2H, J=7.8 Hz), 7.16 (d, 1H, J=4.0 Hz), 7.14 (d, 2H, J=7.6 Hz), 7.08 (d, 1H, J=3.9 Hz), 7.03 (d, 1H, J=7.3 Hz) and 6.98 (d, 2H, J=8.7 Hz); $^{13}$C NMR (CDCl$_3$): δ 182.3, 148.6, 147.4, 146.3, 142.9, 141.1, 137.4, 135.3, 133.7, 131.1, 129.3, 128.5, 127.3, 127.2, 126.9, 126.6, 126.5, 126.4, 126.3, 126.1, 124.0, 123.6, 122.9, 122.8, 122.7 and 120.9; HRMS (m/z): 487.1068 (M$^+$) (calculated value: 487.1065).

Synthesis of 5-(5'-(p-diphenylaminophenyl) thiophen-2'-yl)thiophene-2-carbaldehyde (8P)

Compound 8P was synthesized in a procedure similar to that for 8N except that compound 6N was replaced by 6P in the same mole number, giving compound 8P as yellow solid in 68% yield.

The spectroscopic data of 8P were as follows: $^1$H NMR (CDCl$_3$): δ 9.84 (s, 1H), 7.65 (d, 1H, J=3.9 Hz), 7.45 (d, 2H, J=8.3 Hz), 7.22-7.31 (m, 6H) and 7.04-7.17 (m, 9H); $^{13}$C NMR (CDCl$_3$): δ 182.3, 148.0, 147.3, 147.2, 146.2, 141.2, 137.1, 134.0, 129.3, 127.1, 127.0, 126.5, 124.7, 123.6, 123.4, 123.1 and 123.0; HRMS (m/z): 437.0912 (M$^+$) (calculated value: 437.0809).

Synthesis of 5-(5'-(5"-bromothiophen-2"-yl) thiophen-2'-yl)-2-(naphthylphenylamino)-thiophene (9N)

Compound 9N was synthesized in a procedure similar to that for 2N except that 4,4'-dibromobiphenyl was replaced by 2,5-bis(5'-bromothiophen-2'-yl)thiophene in the same mole number, giving compound 9N as yellow solid in 47% yield.

The spectroscopic data of 9N were as follows: $^1$H NMR (CDCl$_3$): δ 8.02 (d, 1H, J=8.3 Hz), 7.86 (d, 1H, J=8.2 Hz), 7.42-7.52 (m, 4H), 7.21 (t, 2H, J=7.9 Hz), 7.04 (d, 2H, J=8.2 Hz), 6.85-6.97 (m, 6H) and 6.52 (d, 1H, J=4.0 Hz); $^{13}$C NMR (CDCl$_3$): δ 151.8, 148.5, 142.8, 138.7, 137.2, 135.1, 134.0, 130.7, 130.6, 129.0, 128.4, 127.4, 126.7, 126.4, 126.3, 126.2, 125.7, 124.4, 123.8, 123.6, 123.0, 122.4, 121.6, 119.1, 118.5, 117.8 and 110.6; HRMS (m/z): 542.9774 (M$^+$) (calculated value: 542.9785).

Synthesis of 5-(5'-(5"-bromothiophen-2"-yl) thiophen-2'-yl)-2-diphenylamino-thiophene (9P)

Compound 9P was synthesized in a procedure similar to that for 9N except that N-(1-naphthyl)aniline was replaced by N-phenylaniline in the same mole number, giving compound 9P as yellow solid in 50% yield.

The spectroscopic data of 9P were as follows: $^1$H NMR (CDCl$_3$): δ 7.24-7.27 (m, 4H), 7.14-7.16 (m, 4H), 7.03 (t, 2H, J=7.3 Hz), 6.94 (d, 1H, J=3.8 Hz), 6.93 (d, 1H, J=3.8 Hz), 6.91 (d, 1H, J=3.8 Hz), 6.89 (d, 1H, J=3.8 Hz), 6.85 (d, 1H, J=3.8 Hz) and 6.55 (d, 1H, J=3.8 Hz); $^{13}$C NMR (CDCl$_3$): δ 151.0, 147.4, 138.6, 137.1, 134.2, 130.6, 130.3, 129.2, 124.4, 123.4, 123.3, 123.2, 122.7, 122.4, 120.7 and 110.7; HRMS (m/z): 492.9628 (M$^+$) (calculated value: 492.9628).

Synthesis of 5-(5'-(5"-(naphthylphenylamino) thiophen-2"-yl)-thiophen-2'-yl)-thiophene-2-carbaldehyde (10N)

To a three-necked flask containing a solution of compound 9N (0.94 g=1.73 mmol) in dry THF was added dropwise BuLi (2.6 mmol, 1.6 M in a hexane solution of 1.6 mL) at −78° C. The solution was allowed to warm up gradually to 0° C. for about 30 minutes. The solution was cooled again to −78° C., then to it was added dropwise DMF (0.2 mL=2.6 mmol). The reaction solution was warmed up to room temperature and stirred with a magnetic bar overnight. The reaction was quenched by adding distilled water and then extracted by CH$_2$Cl$_2$. The organic layers were combined and dried over anhydrous MgSO$_4$. The solvent was evaporated in vacuo to yield a crude product, which was purified by a silica gel column eluted with CH$_2$Cl$_2$/hexane (1/1) to obtain compound 10N as yellow solid in 72% yield (0.61 g=1.24 mmol).

The spectroscopic data of 10N were as follows: $^1$H NMR (CDCl$_3$): δ 9.82 (s, 1H), 8.01 (d, 1H, J=8.2 Hz), 7.91 (d, 1H, J=8.0 Hz), 7.83 (d, 1H, J=7.6 Hz), 7.61 (d, 1H, J=4.0 Hz), 7.43-7.53 (m, 4H), 7.14-7.25 (m, 4H), 7.06-7.08 (m, 2H), 6.93-6.98 (m, 2H), 6.88 (d, 1H, J=3.9 Hz) and 6.49 (d, 1H, J=3.9 Hz); $^{13}$C NMR (CDCl$_3$): δ 182.2, 152.8, 148.3, 147.0, 142.8, 141.2, 139.8, 137.3, 135.1, 133.2, 130.6, 129.1, 128.4, 127.8, 127.5, 126.9, 126.8, 126.4, 126.3, 126.2, 123.6, 123.5, 123.3, 123.2, 121.9, 119.5 and 117.8; HRMS (m/z): 493.0620 (M$^+$) (calculated value: 493.0629).

Synthesis of 5-(5'-(5"-(diphenylamino)thiophen-2"-yl)thiophen-2'-yl)thiophene-2-carbaldehyde (10P)

Compound 10P was synthesized in a procedure similar to that for 10N except that compound 9N was replaced by 9P in the same mole number, giving 10P as yellow solid in 60% yield.

The spectroscopic data of 10P were as follows: $^1$H NMR (CDCl$_3$): δ 9.81 (s, 1H), 7.60 (d, 1H, J=4.0 Hz), 7.26-7.29 (m, 4H), 7.15-7.19 (m, 6H), 7.0 (t, 2H, J=7.3 Hz), 6.97 (d, 1H, J=3.6 Hz), 6.93 (d, 1H, J=3.8 Hz) and 6.55 (d, 1H, J=3.8 Hz); $^{13}$C NMR (CDCl$_3$): δ 182.2, 152.0, 147.4, 146.9, 141.3, 139.7, 137.3, 133.5, 129.3, 123.8, 123.7, 123.6, 123.0 & 120.1; HRMS (m/z): 443.0472 (M$^+$) (calculated value: 443.0472).

Synthesis of (E)-2-cyano-3-(naphthylphenylamino) triphenylene)acrylic Acid (1N—PPP)

A mixture of compound 3N (242 mg=0.51 mmol), cyanoacetic acid (52 mg=0.61 mmol) and ammonium acetate (10 mg=0.13 mmol) in acetic acid was placed in a three-necked flask under N$_2$-atmosphere and stirred at 120° C. for 12 hours. After cooling, the reaction was quenched by adding water and then extracted by CH$_2$Cl$_2$. The organic layer was dried over anhydrous MgSO$_4$ and the solvent evaporated under vacuum. The products were purified by a silica gel column eluted with CH$_2$Cl$_2$/acetic acid (19/1). The orange solid was isolated in 70% yield (195 mg=0.36 mmol).

The spectroscopic data of 1N—PPP were as follows: $^1$H NMR (DMSO-d$_6$): δ 8.29 (s, 1H), 8.06 (d, 2H, J=8.4 Hz), 7.95 (d, 1H, J=8.2 Hz), 7.81-7.86 (m, 4H), 7.73 (d, 2H, J=8.3 Hz), 7.63 (d, 2H, J=8.3 Hz), 7.43-7.51 (m, 4H), 7.34 (t, 1H, J=7.6 Hz), 7.30 (d, 1H, J=7.2 Hz), 7.17 (t, 2H, J=7.8 Hz) and 6.86-6.95 (m, 5H); $^{13}$C NMR (DMSO-d$_6$): δ 163.8, 154.0, 148.0, 147.7, 144.2, 142.8, 140.1, 137.0, 135.3, 131.8, 130.8, 129.8, 129.0, 127.7, 127.4, 127.3, 126.9, 123.8, 122.7, 122.4, 121.1, 116.7 and 103.5; HRMS (m/z): 542.1992 (M$^+$) (calculated value: 542.1994).

Synthesis of (E)-2-cyano-3-(5'-(4"-(naphthylphenylamino)biphenylene)thiophen-2'-yl)acrylic Acid (1N—PPS)

Compound 1N—PPS was synthesized in a procedure similar to that for 1N—PPP except that compound 3N was replaced by 4N in the same mole number, being obtained as red solid in 65% yield.

The spectroscopic data of 1N—PPS were as follows: $^1$H NMR (DMSO-d$_6$): δ 8.36 (s, 1H), 7.94 (d, 1H, J=8.2 Hz), 7.86 (d, 1H, J=4.1 Hz), 7.84 (d, 1H, J=8.4 Hz), 7.78 (d, 1H, J=8.4 Hz), 7.67 (d, 2H, J=8.3 Hz), 7.62 (d, 1H, J=4.0 Hz), 7.57 (d, 2H, J=8.4 Hz), 7.42-7.50 (m, 4H), 7.33 (t, 1H, J=7.6 Hz), 7.27 (d, 1H, J=7.3 Hz), 7.17 (t, 2H, J=7.8 Hz), 6.90-6.94 (m, 3H) and 6.83 (d, 2H, J=8.6 Hz); $^{13}$C NMR (DMSO-d$_6$): δ 164.2, 152.3, 148.1, 147.5, 146.1, 142.7, 141.0, 140.8, 135.3, 134.9, 131.7, 131.0, 130.9, 129.8, 129.0, 127.7, 127.3, 127.1, 127.0, 126.9, 126.7, 125.1, 123.7, 122.8, 122.5, 120.9, 117.2 and 99.9; HRMS (m/z): 548.1555 (M$^+$) (calculated value: 548.1158).

Synthesis of (E)-2-cyano-3-(p-(5'-(p-(naphthylphenylamino)phenyl)thiophen-2'-yl)-phenyl)acrylic Acid (1N—PSP)

Compound 1N—PSP was synthesized in a procedure similar to that for 1N—PPP except that 3N was replaced by 7N in the same mole number, being obtained as black solid in 61% yield.

The spectroscopic data of 1N—PSP were as follows: $^1$H NMR (DMSO-d$_6$): δ 8.17 (s, 1H), 8.00 (d, 3H, J=7.7 Hz), 7.91 (d, 1H, J=8.3 Hz), 7.80-7.83 (m, 3H), 7.67 (d, 1H, J=3.9 Hz), 7.37-7.59 (m, 7H), 7.26 (t, 2H, J=7.9 Hz), 6.99-7.03 (m, 3H) and 6.86 (d, 2H, J=8.7 Hz); $^{13}$C NMR (DMSO-d$_6$): δ 164.2, 151.9, 148.2, 147.4, 145.1, 142.5, 140.2, 137.6, 135.3, 131.6, 129.8, 129.0, 127.4, 127.1, 127.0, 126.8, 125.6, 123.1, 122.7, 120.8, 117.6 and 105.8; HRMS (m/z): 548.1555 (M$^+$) (calculated value: 548.1158); elementary analysis: C=78.77, H=4.45, N=5.09, O=5.85, S=5.84 (calculated values: C=78.81, H=4.41, N=5.11, O=5.83, S=5.84).

Synthesis of (E)-2-cyano-3-(5'-(5''-(p-(naphthylphenylamino)phenyl)thiophen-2''-yl)-thiophen-2'-yl)acrylic Acid (1N—PSS)

Compound 1N—PSS was synthesized in a procedure similar to that for 1N—PPP except that 3N was replaced by 8N in the same mole number, being obtained as black solid in 67% yield.

The spectroscopic data of 1N—PSS were as follows: $^1$H NMR (DMSO-d$_6$): δ 8.28 (s, 1H), 7.98 (d, 1H, J=8.1 Hz), 7.89 (d, 1H, J=8.2 Hz), 7.78-7.81 (m, 2H), 7.54 (t, 1H, J=7.8 Hz), 7.44-7.49 (m, 5H), 7.39 (t, 1H, J=7.6 Hz), 7.33 (d, 2H, J=4.5 Hz), 7.23 (t, 2H, J=7.8 Hz), 6.96-7.01 (m, 3H) and 6.81 (d, 2H, J=8.6 Hz); $^{13}$C NMR (DMSO-d$_6$): δ 164.6, 148.4, 147.3, 145.4, 144.5, 144.3, 142.5, 139.9, 135.3, 134.5, 133.4, 130.9, 129.9, 129.0, 128.2, 127.7, 127.5, 127.2, 127.1, 126.9, 126.8, 125.8, 124.8, 124.3, 123.6, 123.2, 122.9, 120.5, 118.0 and 102.7; HRMS (m/z): 554.1135 (M$^+$) (calculated value: 554.1123); elementary analysis: C=73.59, H=4.05, N=5.07, O=5.76 and S=11.53 (calculated values: C=73.62, H=4.00, N=5.05, O=5.77 and S=11.56).

Synthesis of (E)-2-cyano-3-(5'-(5''-(5'''-(naphthylphenylamino)-thiophen-2'''-yl)-thiophen-2''-yl)thiophen-2'-yl)acrylic Acid (1N—SSS)

Compound 1N—SSS was synthesized in a procedure similar to that for 1N—PPP except that 3N was replaced by 10N in the same mole number, being obtained as black solid in 55% yield.

The spectroscopic data of 1N—SSS were as follows: $^1$H NMR (DMSO-d$_6$): δ 8.30 (s, 1H), 7.99 (d, 1H, J=8.1 Hz), 7.93 (d, 1H, J=8.2 Hz), 7.86 (d, 1H, J=8.2 Hz), 7.78 (d, 1H, J=3.6 Hz), 7.46-7.58 (m, 4H), 7.40 (dd, 1H, J=3.8, 0.9 Hz), 7.37 (dd, 1H, J=3.8, 0.9 Hz), 7.20 (t, 2H, J=7.5 Hz), 7.09 (dd, 1H, J=3.8, 0.9 Hz), 7.06 (dd, 1H, J=3.8, 0.9 Hz), 6.93 (d, 3H, J=7.9 Hz) and 6.50 (dd, 1H, J=3.9, 1.0 Hz); $^{13}$C NMR (DMSO-d$_6$): δ 164.3, 152.5, 148.0, 145.0, 144.6, 142.4, 140.5, 138.9, 135.2, 134.4, 132.9, 130.3, 130.0, 129.8, 129.1, 128.2, 128.1, 127.5, 127.3, 127.0, 124.9, 124.6, 124.5, 123.2, 122.5, 119.4, 118.3, 117.7 and 101.2; HRMS (m/z): 560.0694 (M$^+$) (calculated value: 560.0687); elementary analysis: C=68.60, H=3.63, N=4.98, O=5.73 and S=17.15 (calculated values: C=68.55, H=3.60, N=5.00, O=5.71 and S=17.16).

Synthesis of (E)-2-cyano-3-(diphenylaminotriphenylene)acrylic Acid (1P—PPP)

Compound 1P—PPP was synthesized in a procedure similar to that for 1N—PPP except that 3N was replaced by 3P in the same mole number, being obtained as orange solid in 64% yield.

The spectroscopic data of 1P—PPP were as follows: $^1$H NMR (DMSO-d$_6$): δ 8.33 (s, 1H), 8.11 (d, 2H, J=8.5 Hz), 7.92 (d, 2H, J=8.5 Hz), 7.83 (d, 2H, J=8.5 Hz), 7.73 (d, 2H, J=8.5 Hz), 7.63 (d, 2H, J=6.8 Hz), 7.29 (t, 4H, J=7.0 Hz) and 7.00-7.06 (m, 8H); $^{13}$C NMR (DMSO-d$_6$): δ 163.7, 154.1, 147.4, 147.3, 144.2, 140.1, 137.2, 133.2, 131.8, 130.8, 130.0, 127.9, 127.8, 127.4, 124.7, 123.8, 123.4, 116.7 and 103.4; HRMS (m/z): 492.1830 (M$^+$) (calculated one: 492.1838); elementary analysis: C=82.87, H=4.93, N=5.65, O=6.55 (calculated values: C=82.91, H=4.91, N=5.69, O=6.50).

Synthesis of (E)-2-cyano-3-(5'-(diphenylaminobiphenylene)thiophen-2'-yl)acrylic Acid (1P—PPS)

Compound 1P—PPS was synthesized in a procedure similar to that for 1N—PPP except that 3N was replaced by 4P in the same mole number, being obtained as black solid in 61% yield.

The spectroscopic data of 1P—PPS were as follows: $^1$H NMR (DMSO-d$_6$): δ 8.05 (s, 1H), 7.95 (d, 2H, J=7.4 Hz), 7.80 (d, 2H, J=8.2 Hz), 7.66 (d, 1H, J=3.7 Hz), 7.59 (d, 2H, J=8.7 Hz), 7.44 (d, 1H, J=3.8 Hz), 7.31 (t, 4H, J=7.9 Hz), 7.02-7.08 (m, 6H) and 6.96 (d, 2H, J=8.7 Hz); $^{13}$C NMR (DMSO-d$_6$): δ 164.3, 148.3, 147.5, 147.1, 144.4, 140.8, 136.4, 132.0, 130.8, 130.0, 127.5, 126.9, 126.8, 125.6, 124.8, 124.6, 123.9, 123.2 and 119.1; HRMS (m/z): 498.1395 (M$^+$) (calculated: 498.1402); elementary analysis: C=77.13, H=4.49, N=5.59, O=6.45 and S=6.34 (calculated values: C=77.09, H=4.45, N=5.62, O=6.42 and S=6.43).

Synthesis of (E)-2-cyano-3-(p-(5'-(p-diphenylamino)phenyl)-thiophen-2'-yl)phenyl)-acrylic Acid (1P—PSP)

Compound 1P—PSP was synthesized in a procedure similar to that for 1N—PPP except that 3N was replaced by 7P in the same mole number, being obtained as black solid in 70% yield.

The spectroscopic data of 1P—PSP were as follows: $^1$H NMR (DMSO-d$_6$): δ 8.22 (s, 1H), 7.80 (d, 1H, J=3.7 Hz), 7.77 (d, 2H, J=8.3 Hz), 7.71 (d, 2H, J=8.3 Hz), 7.67 (d, 1H, J=3.7 Hz), 7.62 (d, 2H, J=8.5 Hz), 7.30 (t, 4H, J=7.6 Hz) and 6.99-7.06 (m, 8H); $^{13}$C NMR (DMSO-d$_6$): δ 164.2, 149.1, 147.5, 147.3, 140.3, 137.6, 136.2, 133.1, 131.6, 130.0, 127.9, 127.2, 126.8, 124.9, 124.7, 123.8, 123.4 and 119.1; HRMS (m/z): 498.1395 (M$^+$) (calculated value: 498.1402); elementary analysis: C=77.03, H=4.51, N=5.57, O=6.49, S=6.40 (calculated ones: C=77.09, H=4.45, N=5.62, O=6.42, S=6.43).

Synthesis of (E)-2-cyano-3-(5'-(5"-(p-(diphenylamino)phenyl)-thiophen-2"-yl)-thiophen-2'-yl) acrylic Acid (1P—PSS)

Compound 1P—PSS was synthesized in a procedure similar to that for 1N—PPP except that 3N was replaced by 8P in the same mole number, being obtained as black solid in 69% yield.

The spectroscopic data of 1P—PSS were as follows: $^1$H NMR (DMSO-$d_6$): δ 8.24 (s, 1H), 7.74 (d, 1H, J=3.8 Hz), 7.50 (d, 2H, J=8.4 Hz), 7.44 (d, 1H, J=3.7 Hz), 7.41 (d, 1H, J=3.8 Hz), 7.35 (d, 1H, J=3.8 Hz), 7.26 (t, 4H, J=7.2 Hz), 7.02 (t, 4H, J=7.2 Hz), 6.97 (d, 2H, J=7.5 Hz) and 6.87 (d, 2H, J=7.5 Hz); $^{13}$C NMR (DMSO-$d_6$): δ 164.7, 147.8, 147.0, 145.2, 144.4, 144.3, 139.9, 134.6, 133.7, 130.1, 128.1, 126.9, 126.8, 124.9, 124.8, 124.6, 124.1, 122.8, 118.0 and 102.6; HRMS (m/z): 504.0967 (M$^+$) (calculated value: 504.0966); elementary analysis: C=71.38, H=4.01, N=5.51, O=6.37 and S=12.73 (calculated values: C=71.40, H=3.99, N=5.55, O=6.34 and S=12.71).

Synthesis of (E)-2-cyano-3-(5'-(5"-(5'''-(diphenylamino)-thiophen-2'''-yl)thiophen-2"-yl)thiophen-2'-yl)acrylic Acid (1P—SSS)

Compound 1P—SSS was synthesized in a procedure similar to that for 1N—PPP except that 3N was replaced by 10P in the same mole number, being obtained as black solid in 60% yield.

The spectroscopic data of 1P—SSS were as follows: $^1$H NMR (DMSO-$d_6$): δ 8.31 (s, 1H), 7.80 (d, 1H, J=4.1 Hz), 7.42 (d, 1H, J=4.0 Hz), 7.41 (d, 1H, J=3.9 Hz), 7.28 (t, 4H, J=3.9 Hz), 7.14 (d, 1H, J=3.93 Hz), 7.13 (d, 1H, J=3.9 Hz), 7.05-7.07 (m, 6H) and 6.53 (d, 1H, J=4.0 Hz); $^{13}$C NMR (DMSO-$d_6$): δ 164.1, 151.7, 147.1, 145.7, 145.0, 141.1, 139.0, 134.3, 130.0, 128.6, 128.3, 125.1, 124.8, 124.6, 124.4, 123.2, 120.5, 117.4 and 100.0; HRMS (m/z): 510.0537 (M$^+$) (calculated value: 510.0530); elementary analysis: C=65.80, H=3.60, N=5.45, O=6.31 and S=18.84 (calculated values: C=65.86, H=3.55, N=5.49, O=6.27 and S=18.84).

Properties of the Compounds

The absorption spectra of the compounds synthesized as above were recorded on a Hewlett-Packard 8453 spectrofluorometer. The redox potentials of the same were measured with cyclic voltammetry on a CHI 620 analyzer.

Further analyses of the compound structures were done with quantum chemistry computation using the Q-Chem 3.0 software, where the structures were optimized using B3LYP/6-31G* hybrid functional. For the excited states, a time-dependent density functional theory (TDDFT) with the B3LYP functional was employed. The frontier orbital plots of the highest occupied molecular orbitals (HOMOs) and the lowest unoccupied molecular orbitals (LUMOs) were drawn by using Gaussian 03.

The absorption spectra of the compounds in THF solution were shown in FIG. 1. Each of these compounds exhibits a major absorption band on the long wavelength edge at $\lambda_{max}$ 380~480 nm. This band exhibits a distinctive solvent shift, and is thus assigned a π–π* transition mixed with significant CT character (ESI). Upon photo excitation, the high-lying electron, mostly localized on the triarylamine (D) moiety, migrates to cyanoacrylic acid (A) on the other side of the molecule. The electron movement is heavily coupled with the π-orbitals of the central triarylene linkage (B). The linkages containing more thiophene moieties displayed a greater bathochromic shift, e.g. SSS≈PSS>PSP≈PPS>PPP in both two series.

The high-lying r-orbital in thiophene is located at a higher potential level than that in a phenyl ring, and is therefore delocalized more extensively than the latter. A better conjugation in the former is also supported by a more planar conformation. For example, the dihedral angle between adjacent aryl rings is nearly zero in SSS type structure, yet is significantly twisted (~36°) in the PPP type as estimated by molecular modeling. The molar extinction coefficients (2-4×10$^4$ M$^{-1}$cm$^{-1}$) of all compounds are not much different from each other, yet are all higher than that of the well known ruthenium dyes (<2×10$^4$ M$^{-1}$cm$^{-1}$). It is also noteworthy in FIG. 1 that the absorption intensity of a 1N-series compound (thick line) is consistently higher than that of the corresponding 1P-series compound (thin line). This phenomenon seems to correspond well with the better performance of DSSC devices made with the former materials.

Figure 2:
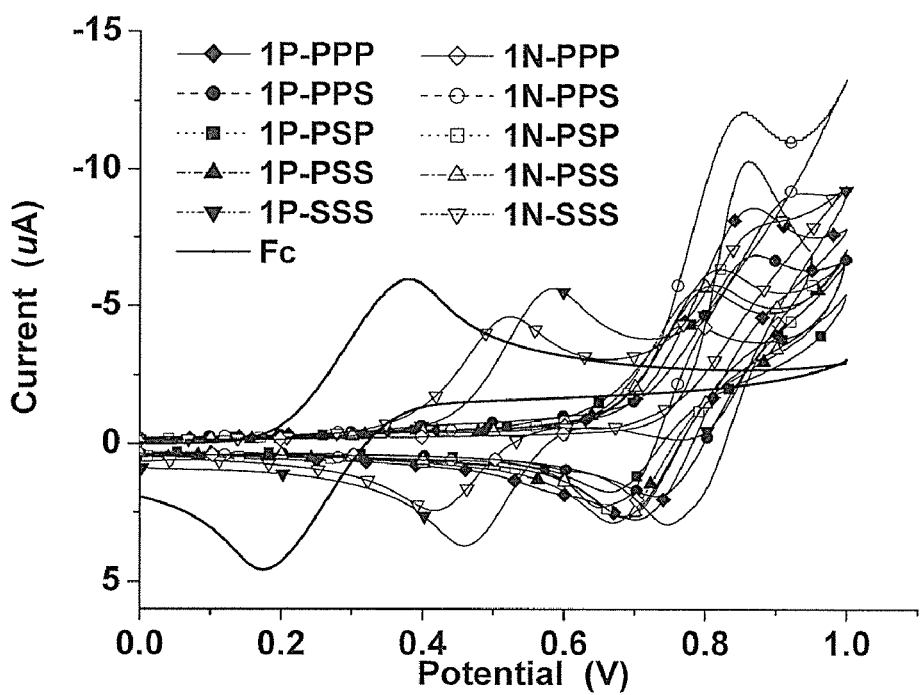
FIG. 2 shows the oxidative voltammograms of the dye compounds in Example 1.

The first oxidation potentials ($E_{ox}$), corresponding to the HOMO level of dyes, were measured by cyclic voltammetry (CV) in THF (FIG. 2) and the results summarized in Table 1. The LUMO levels were estimated by the values of $E_{ox}$ and the 0-0 band gaps, wherein the latter were obtained at the intersection of absorption and emission spectra. The band gap energies reduce along with the number of thiophene units, i.e., the band gaps arranged in the order of 1P—PPP (2.77) 1P—PSP (2.53)≈1P—PPS (2.54) 1P—PSS (2.30)≈1P—SSS (2.24), and 1N—PPP (2.78) 1N—PSP (2.52)≈1N—PPS (2.52) 1N—PSS (2.32) 1N—SSS (2.16). The oxidation waves of both 1P—SSS and 1N—SSS exhibit two maxima, which indicate clearly that the amine π-orbital resonates significantly with nearby thiophene π-orbital. The interaction pushes up the potential energy level of the amine donor, thereby lowers its oxidation potential. The estimated LUMO levels of all dyes are sufficiently higher than the electron injection level of TiO$_2$ (~−0.5 V), while their HOMO levels are sufficiently lower than that of the electrolyte pair I$^-$/I$_3^-$ (~0.4 V). Such electronic structures thus ensure a favorable exothermic flow of charges throughout the photo-electronic conversion.

TABLE 1

Calculated (TDDFT/B3LYP) and experimental parameters for the 1N-series and 1P-series dye compounds.

| Dye | HOMO/LUMO$^a$ (eV) | Band gap$^a$ | f$^a$ | $\lambda_{abs}^b$ (nm)/ (ε (M$^{-1}$ cm$^{-1}$)) | $E_{0-0}^b$ (eV) | $E_{ox}^c$ (V) | $E_{HOMO}/E_{LUMO}^d$ (V) | $J_{sc}$ (mA·cm$^{-2}$) | $V_{oc}$ (V) | FF | η$^e$ (%) |
|---|---|---|---|---|---|---|---|---|---|---|---|
| 1P-PPP | −5.08/−2.57 | 2.50 | 0.28 | 380 (30200) | 2.77 | 0.85 | 5.35/2.58 | 11.43 | 0.65 | 0.62 | 4.58 |
| 1P-PPS | −5.09/−2.64 | 2.45 | 0.41 | 417 (23000) | 2.54 | 0.86 | 5.36/2.82 | 13.86 | 0.65 | 0.57 | 5.14 |
| 1P-PSP | −5.06/−2.61 | 2.45 | 0.71 | 427 (29000) | 2.53 | 0.79 | 5.29/2.77 | 15.36 | 0.69 | 0.50 | 5.25 |
| 1P-PSS | −5.08/−2.69 | 2.38 | 0.85 | 461 (27100) | 2.30 | 0.79 | 5.29/2.99 | 16.26 | 0.66 | 0.58 | 6.17 |
| 1P-SSS | −5.02/−2.72 | 2.29 | 0.96 | 468 (22500) | 2.24 | 0.58 | 5.08/2.84 | 10.89 | 0.58 | 0.60 | 3.75 |

TABLE 1-continued

Calculated (TDDFT/B3LYP) and experimental parameters for the 1N-series and 1P-series dye compounds.

| Dye | HOMO/LUMO$^a$ (eV) | Band gap$^a$ | f$^a$ | $\lambda_{abs}{}^b$ (nm)/ ($\epsilon$ (M$^{-1}$ cm$^{-1}$)) | $E_{0\text{-}0}{}^b$ (eV) | $E_{ox}{}^c$ (V) | $E_{HOMO}/E_{LUMO}{}^d$ (V) | $J_{sc}$ (mA·cm$^{-2}$) | $V_{oc}$ (V) | FF | $\eta^e$ (%) |
|---|---|---|---|---|---|---|---|---|---|---|---|
| 1N-PPP | −5.10/−2.59 | 2.51 | 0.26 | 375 (37400) | 2.78 | 0.83 | 5.33/2.55 | 11.24 | 0.68 | 0.60 | 4.60 |
| 1N-PPS | −5.08/−2.60 | 2.48 | 0.44 | 422 (36300) | 2.52 | 0.82 | 5.32/2.80 | 14.20 | 0.66 | 0.60 | 5.68 |
| 1N-PSP | −5.12/−2.63 | 2.49 | 0.77 | 422 (37700) | 2.52 | 0.82 | 5.32/2.80 | 16.81 | 0.74 | 0.57 | 7.08 |
| 1N-PSS | −5.11/−2.70 | 2.41 | 0.83 | 461 (31300) | 2.32 | 0.81 | 5.31/2.99 | 14.28 | 0.71 | 0.60 | 6.12 |
| 1N-SSS | −4.99/−2.69 | 2.30 | 1.03 | 480 (22200) | 2.16 | 0.53 | 5.03/2.87 | 11.88 | 0.58 | 0.54 | 3.74 |
| N719 | — | — | — | — | — | — | — | 17.68 | 0.75 | 0.61 | 7.64 | f: Oscillator Strength for the lowest energy transition;
$\epsilon$: absorption coefficient;
$E_{ox}$: oxidation potential;
$E_{0\text{-}0}$: 0-0 transition energy measured at the intersection of absorption and emission spectra;
$J_{sc}$: short-circuit photocurrent density;
$V_{oc}$: open-circuit photovoltage;
FF: fill factor;
$\eta$: total power conversion efficiency.
$^a$TDDFT/B3LYP calculated values.
$^b$in THF.
$^c$Oxidation potential in THF (10$^{-3}$ M) containing 0.1 M (n-C$_4$H$_9$)$_4$NPF$_6$ with a scan rate 100 mV·s$^{-1}$.
$^d$E$_{HOMO}$ was calculated by E$_{ox}$ + 4.5 V (vs. NHE), and E$_{LUMO}$ = E$_{HOMO}$ − E$_{0\text{-}0}$.
$^e$Performance of DSSC measured in a 0.25 cm$^2$ working area on a FTO (15 Ω/square) substrate.

The electronic configurations were further examined by theoretical models implanted in Gaussian03 program. Their molecular geometries were optimized by using B3LYP/6-31G* basis set first, then the orbitals of both ground and excited states were computed by time-dependent density functional theory (TDDFT) with B3LYP functional. According to the optimized molecular geometry, the conformation of two adjacent thiophene rings is nearly coplanar, but the orientation of two adjacent phenyl rings is twisted to ~36° due to steric hindrance (ESI). As a result, the electronic resonance is transmitted more efficiently through thiophene moieties than through phenyl groups. A better resonance along thiophene moieties leads to a lower band gaps, yet the same effect also promotes the rate of charge recombination which quenches the excited state. The HOMO/LUMO energy levels and band gaps of the dyes are listed in Table 1.

Figure 3:
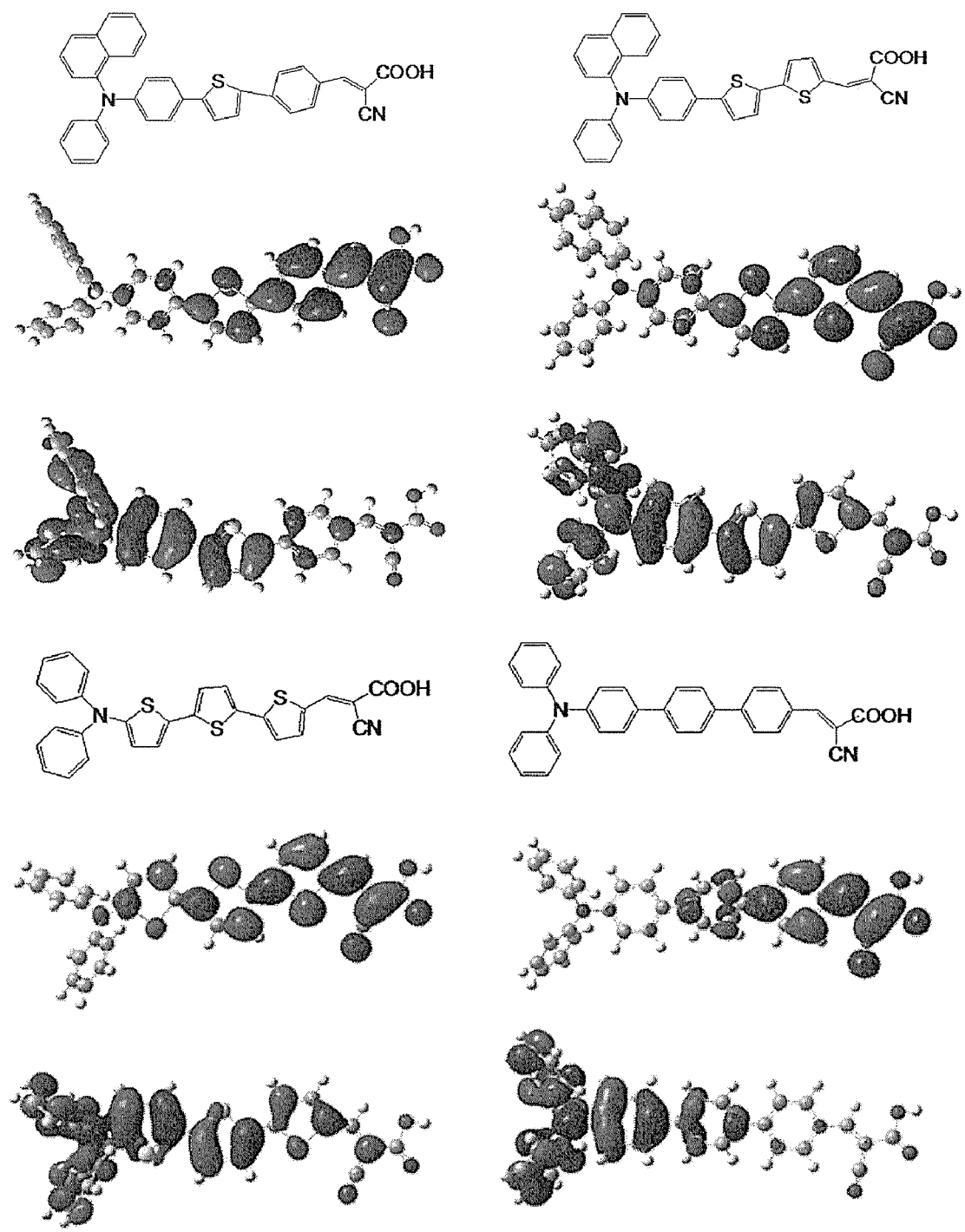
FIG. 3 shows the computed frontier orbitals of compounds 1N—PSP, 1N—PSS, 1P—SSS and 1P—PPP in Example 1, wherein each upper/lower graph shows a LUMO/HOMO.
Figure 4:
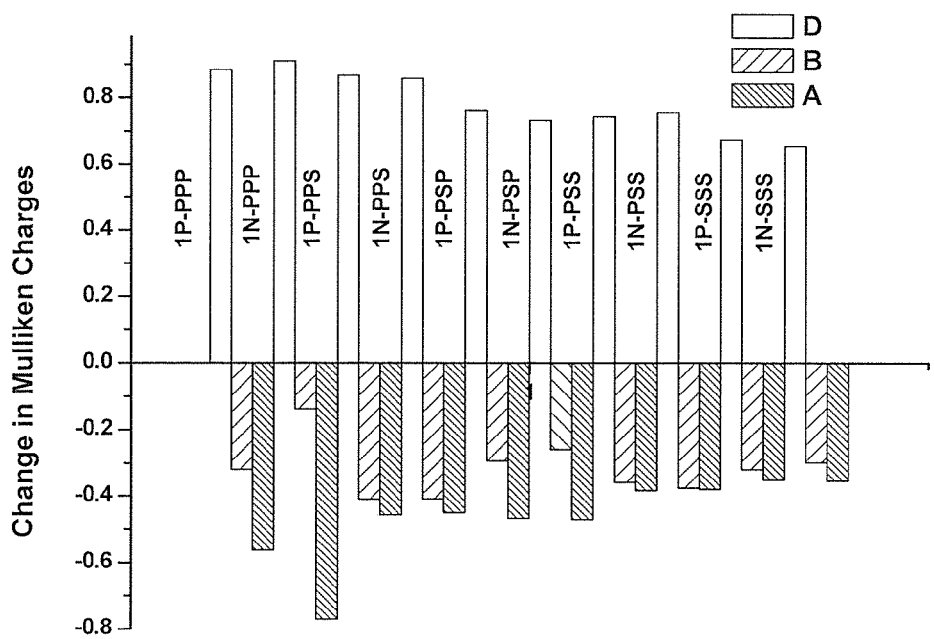
FIG. 4 shows the difference of Mulliken charges between the ground state ($S_0$) and the excited state ($S_1$) of the dye compounds in Example 1, which was estimated by the time dependent DFT/B3LYP model (ESI).

The electronic density distributions before and after photoexcitation can be illustrated better by the graphs in FIGS. 3 and 4. The electron densities in the HOMOs are distributed mainly around the amine moieties (D), and those in the LUMOs around the cyanoacrylic acid moieties (A). Photoexcitation pumps an electron from the HOMO to the LUMO, therefore shifts considerable amount of electron density from D to A. The difference of Mulliken charge density surrounding D, triarylene (B) and A moieties before (S$_0$-state) and after (S$_1$-state) photoexcitation can be depicted by the magnitude of bar charts in FIG. 4. The degree of charge separation declines along with the additional number of thiophenylene groups in the arrays, as a result of more coplanar conformation across the ring junctions. Such a phenomenon can best be demonstrated by a comparison of the HOMO and LUMO orbitals between 1P—SSS and 1P—PPP as shown in FIG. 3. The orbitals delocalize over a wider range through the relay of thiophene groups in the former than they do through the phenylene linkages in the latter.

Performances of the Compounds as Dye Sensitizers

In order to test their performances as dye sensitizers of DSSC, the compounds were further used to fabricate DSSCs, of which the performances were measured.

<Fabrication and Characterization of DSSCs>

A thin film of nanocrystalline anatase TiO$_2$ of 16-18 μm thick was coated on an FTO glass substrate with an area of 0.25 cm$^2$, immersed in a THF solution containing 3×10$^{-4}$ M of dye compound for 12 hours, and then rinsed with anhydrous acetonitrile and dried. Another piece of FTO with a sputtered Pt-film of 100 nm thick was used as a counter electrode. The active area was controlled at a dimension of 0.25 cm$^2$ by adhering a polyester tape of 60 μm thick onto the Pt electrode. The photocathode was placed on top of the counter electrode, and they were tightly clipped together to form a cell. Electrolyte was then injected into the seam between two electrodes. An acetonitrile solution containing LiI (0.5 M), I2 (0.05 M) and 4-t-butylpyridine (0.5 M) was used as the electrolyte. A device made of the commercial dye N719 under the same condition was compared as a reference. The cell parameters were obtained under an incident light with intensity 100 mW·cm$^{-2}$, which was generated by a Xe-lamp of 300 W passing through an AM 1.5 filter. The current-voltage parameters of DSSCs were recorded by a potentiostat/galvanostat model CHI650B (CH Instruments, U.S.A.).

Figure 5:
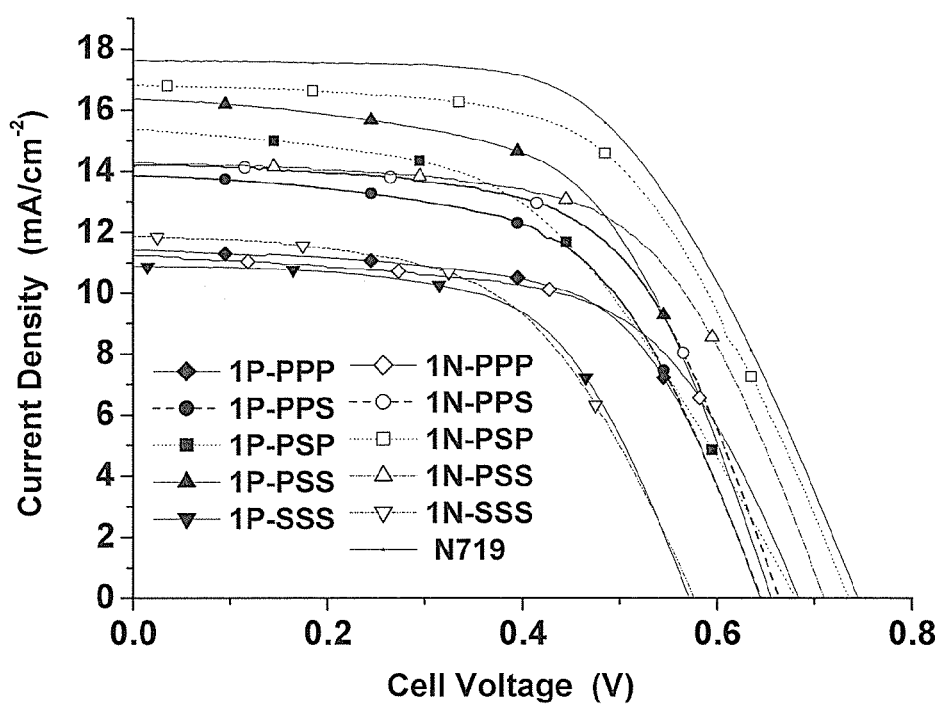
FIG. 5 shows the I-V curves of the compounds of the 1N-series and 1P-series in Example 1.
Figure 6:
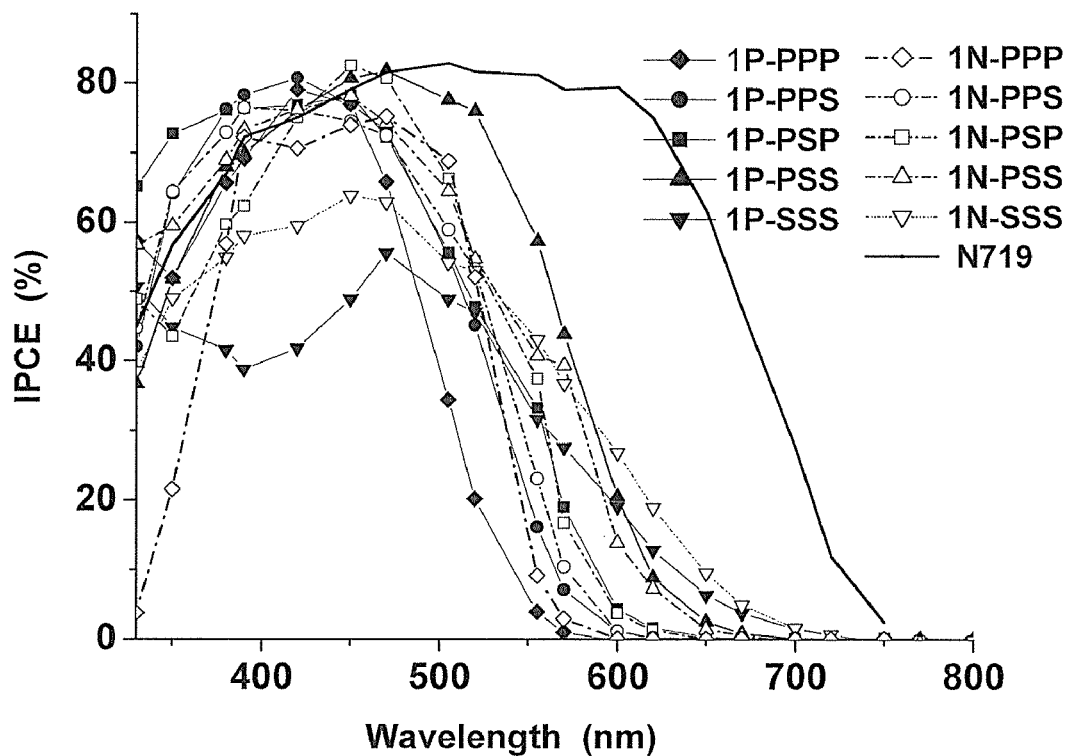
FIG. 6 is the IPCE plots of the compounds of the 1N-series and 1P-series in Example 1.

The photovoltaic performances of the DSSCs fabricated above are summarized in Table 1, and the J-V curves of all dyes are shown in FIG. 5. The current density maintains a constant value within a range of 11-17 mA/cm$^2$ up to 0.4 V. Plots of incident photon to current conversion efficiency (IPCE) at various wavelengths are given in FIG. 6. The active photo-to-current conversion area of these dyes lies in the blue/green region, as implied by their absorption spectra (FIG. 1). Nevertheless, their optimal conversion ratios reach to about 80%, which is quite close to that of N719 at the same wavelengths. Generally speaking, the 1N-series compounds perform relatively better than the 1P-series compounds, which is consistent with the higher absorptivity of the 1N-series compounds as compared with the 1P-series compounds (FIG. 1). The naphthalene substituent may also have provided a better environment for resonance around the nitrogen donor, thus stabilizing the positive charge better. The larger size of naphthalene may also have an effect of increasing the steric hindrance to prevent the material from self-aggregation.

The comparison between the performances of 1P—SSS and 1P—PPP is also worth mentioning. The former exhibited both a lower short-circuit current ($J_{sc}$=10.9 mA·cm$^{-2}$) and a lower open-circuit voltage ($V_{oc}$=0.58 V) than the latter ($J_{sc}$=11.4 mA·cm$^{-2}$; $V_{oc}$=0.65 V). The overall field factor (FF) of the former (0.60) turned out slightly smaller than that of the latter (0.62), which led to a relatively lower quantum efficiency (3.75% vs. 4.58%).

The efficiency of DSSCs indeed depends upon a delicate balance between the degree of electronic resonance and the rate of charge recombination of the organic chromophore. Among all these compounds, the best performance was found in compound 1N—PSP. A device made of this material exhibited a $J_{sc}$-value of 16.81 mA·cm$^{-2}$, a $V_{oc}$-value of 0.74 V and an FF-value of 0.57. The overall conversion efficiency (η) was estimated to be 7.08%, which is quite compatible to the well-known ruthenium complex N-719. The IPCE was higher than 80% within the region of 450-470 nm. Besides 1N—PSP, others like 1P—PSS, 1N—PPS and 1N—PSS also yielded quantum efficiency in the proximity of 6%.

In summary, a series of dipolar compounds containing a triarylene bridge were prepared by convenient methods in this embodiment and can be used as highly efficient dye sensitizers in DSSCs. These compounds exhibited a high absorptivity in the blue/green region of solar light. The DSSC devices fabricated by using these materials as dye sensitizers displayed remarkable quantum efficiency, typically in a range of 5-7%. The optimal IPCE value reaches beyond 80%.

In addition, adjacent phenylene groups are twisted with a large dihedral angle, nevertheless such a twisted conformation retards the charge recombination. A delicate balance need to be tuned between the charge separation and the charge recombination by modifying the molecular structures. The best performance among these compounds was found in 1N—PSP, which showed a maximal IPCE value of 82%, a $J_{sc}$-value of 16.81 mA·cm$^{-2}$, a $V_{oc}$-value of 0.74 V and an FF-value of 0.57, which correspond to an overall conversion efficiency of 7.08%.

Example 2

Among the compounds in which B$^1$ and B$^2$ each independently represent phenyl or naphthyl in which arbitrary hydrogen atom is substituted by a C$_1$-C$_3$ alkyl group or a C$_1$-C$_3$ alkoxy group, the following compounds were synthesized, measured for their properties and tested for their light-harvesting performances as dye sensitizers in DSSCs.

1T-PPP

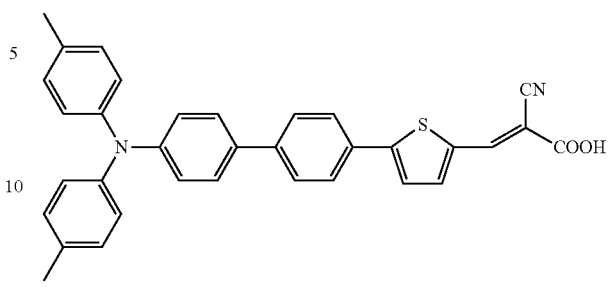

1T-PPS

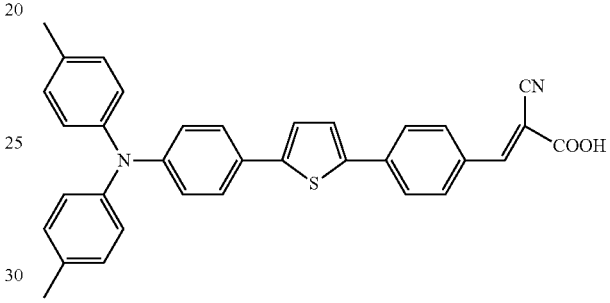

1T-PSP

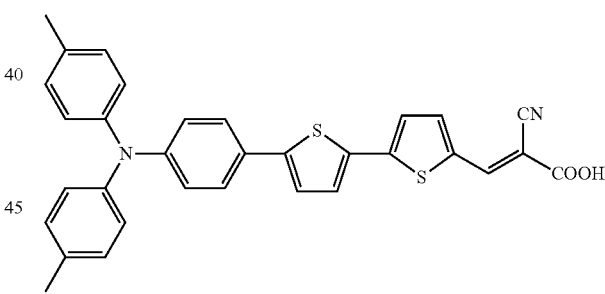

1T-PSS

1T-SSS

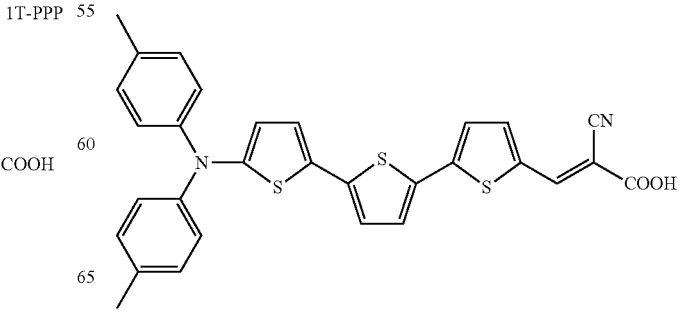

1M-PPP

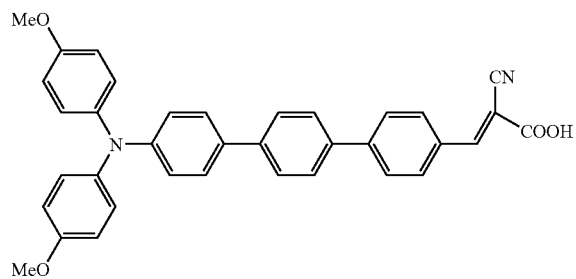

1M-PPS

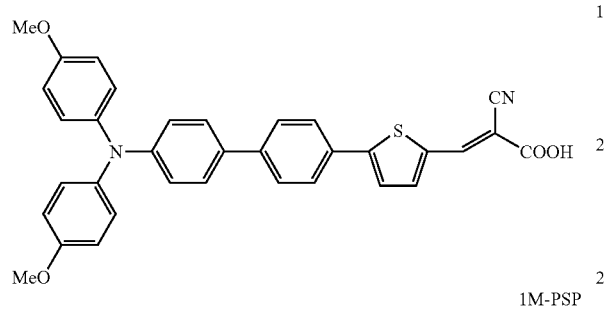

1M-PSP

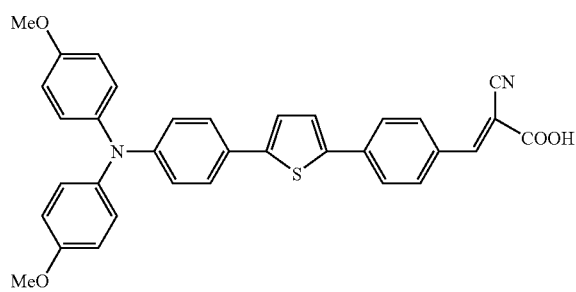

1M-PSS

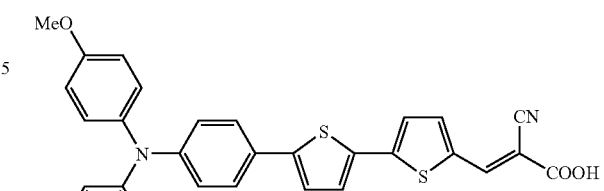

1M-SSS

In the above formulae, "T" and "M" in "1T" and "1M" denote tolyl and methoxyphenyl, respectively, and "P" and "S" are defined as in Example 1.

Syntheses and Characterizations of the Compounds

The synthetic sequences are outlined in Scheme 2, being similar to those shown in Scheme 1. The atmosphere and the solvents for the syntheses, the sources of the reagents, the column type for chromatographic separations and the instruments for compound characterization are the same as those in Example 1. Only the diarylamino compounds as the starting materials were modified as compared with Example 1.

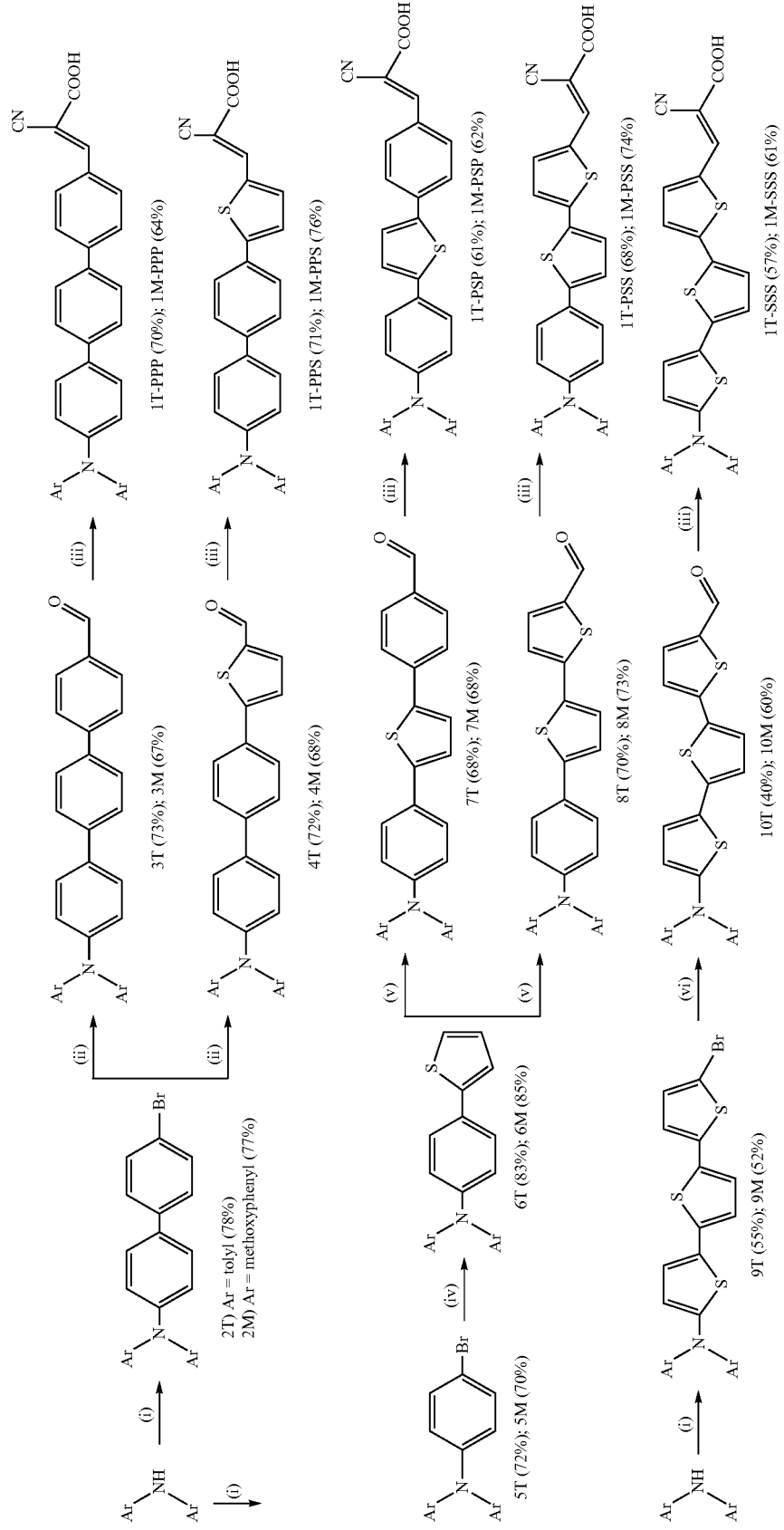

Scheme 2

(i) Pd(OAc)₂/dppf, 4,4'-dibromobiphenyl (2) or 1,4-dibromobenzene (5) or 2,5-bis(5'-bromothiophen-2'-yl)thiophene (9), toluene, 90° C.; (ii) BuLi, triisopropylborate, THF, -78° C. → HCl(aq) → Pd(PPh₃)₄, 4-bromobenzaldehyde (3) or 5-bromothiophene-2-carbaldehyde (4), toluene, K₂CO₃; (iii) cyano-acetic acid, NH₄OAc, AcOH, 90-100° C.; (iv) PdCl₂(PPh₃)₂, 2-(tributylstannyl)thiophene, DMF, 90° C.; (v) BuLi, tributyltin chloride, THF, -78° C. → PdCl₂(PPh₃)₂, 4-bromobenzaldehyde (7) or 5-bromothiophene-2-carbaldehyde (8), DMF; (vi) BuLi, THF, -78° C. → DMF.

Synthesis of 4-bromo-4'-ditolylaminobiphenyl (2T)

A mixture of 4,4'-dibromobiphenyl (8.46 g=27.4 mmol), Pd(OAc)$_2$ (105 mg=0.18 mmol), dppf (253 mg=0.46 mmol), di-p-tolylamine (1.80 g=9.13 mmol) and sodium t-butoxide (1.32 g=13.7 mmol) in dry toluene was placed in a three-necked flask under a nitrogen atmosphere and stirred at 90° C. for 15 h. After cooling, the reaction was quenched by adding water and then extracted by ethyl acetate. The organic layer was dried over anhydrous MgSO$_4$ and evaporated under vacuum. The products were purified by silica gel column eluted with hexane. White solid of compound 2T was obtained in 78% yield (3.04 g=7.12 mmol).

The spectroscopic data of compound 2T were as follows: $^1$H NMR (CDCl$_3$): δ 7.52 (d, 1H, J=8.4 Hz), 7.42 (d, 2H, J=8.6 Hz), 7.40 (d, 2H, J=8.6 Hz), 7.04-7.10 (m, 10H) and 2.35 (s, 6H); $^{13}$C NMR (CDCl$_3$): δ 147.9, 145.0, 139.6, 132.8, 132.6, 131.7, 129.9, 128.1, 127.3, 124.8, 122.4, 120.6 and 20.8; HRMS (m/z): 427.0942 (M$^+$).

Synthesis of 4-bromo-4'-di(methoxyphenyl)aminobiphenyl (2M)

Compound 2M was synthesized in a procedure similar to that for 2T except that di-p-tolylamine was replaced by di(p-methoxyphenyl)amine in the same mole ratio, giving compound 2M as white solid in 77% yield.

The spectroscopic data of compound 2M were as follows: $^1$H NMR (CDCl$_3$): δ 7.52 (d, 1H, J=8.5 Hz), 7.42 (d, 2H, J=8.6 Hz), 7.40 (d, 2H, J=8.6 Hz), 7.04-7.10 (m, 10H) and 3.79 (s, 6H); $^{13}$C NMR (CDCl$_3$): δ 147.9, 145.0, 139.6, 132.8, 132.6, 131.7, 129.9, 128.1, 127.3, 124.8, 122.4, 120.6 and 55.4; HRMS (m/z): 459.0838 (M$^+$).

Synthesis of 4'-(ditolylamino)triphenylene-4-carbaldehyde (3T)

To a three-necked round-bottom flask containing 2T (6.49 g=15.2 mmol) was added dropwise BuLi (16.1 mmol, 1.6 M in a hexane solution of 10 mL) in dry THF at −78° C., and then the solution was brought to 0° C. and stirred by a magnetic bar for 30 minutes. The solution was cooled again to −78° C. and to it was added dropwise tri-isopropyl borate (5.3 mL=19.8 mmol). The reaction solution was warmed up gradually to room temperature and stirred overnight. To the reaction solution was then added excess amount (30 mL) of 10% HCl$_{(aq)}$, while the mixture was stirred for another 1 hour. The reaction was quenched by pouring into distilled water, followed by extraction with ethyl acetate. The organic layer was dried over anhydrous MgSO$_4$, and evaporation of the solvent gave a crude product, which was immediately subjected to the next reaction.

The crude product was mixed with p-bromobenzaldehyde (2.57 g=14.0 mmol), K$_2$CO$_{3(aq)}$ (2.76 g=2 mmol) in 10 mL of H$_2$O, and Pd(PPh$_3$)$_4$ (807 mg=0.69 mmol) in dry toluene/THF (2/1). The mixture was heated to 90° C. for 12 hours. After cooling, the products were extracted by ethyl acetate and the organic layer dried over anhydrous MgSO$_4$. The crude product was dried in vacuo and purifies by a silica gel column eluted with CH$_2$Cl$_2$/hexane (1/1). Yellow solid of compound 3T was obtained in 73% yield (5.03 g=11.1 mmol).

The spectroscopic data of compound 3T were as follows: $^1$H NMR (CDCl$_3$): δ 10.04 (s, 1H), 7.95 (d, 2H, J=8.2 Hz), 7.79 (d, 2H, J=8.2 Hz), 7.64-7.69 (m, 4H), 7.47 (d, 2H, J=8.7 Hz), 7.08 (d, 4H, J=8.5 Hz), 7.03 (dt, 4H, J=8.5, 2.1 Hz) and 2.33 (s, 6H); $^{13}$C NMR (CDCl$_3$): δ 191.7, 147.9, 146.7, 145.0, 140.9, 137.6, 135.1, 132.8, 132.7, 130.2, 129.9, 127.6, 127.4, 127.3, 126.9, 124.8, 122.3 and 20.7; HRMS (m/z): 453.2087 (M$^+$).

Synthesis of 4'-(dimethoxyphenylamino)triphenylene-4-carbaldehyde (3M)

Compound 3M was synthesized in a procedure similar to that of 3T except that compound 2T was replaced by 2M in the same mole number, giving compound 3M as yellow solid in 67% yield.

The spectroscopic data of 3M were as follows: $^1$H NMR (CDCl$_3$): δ 10.03 (s, 1H), 7.93 (d, 2H, J=8.0 Hz), 7.77 (d, 2H, J=8.0 Hz), 7.67 (d, 2H, J=8.6 Hz), 7.64 (d, 2H, J=8.6 Hz), 7.46 (d, 2H, J=8.4 Hz), 7.10 (d, 4H, J=8.4 Hz), 7.00 (d, 2H, J=8.2 Hz), 6.85 (d, 4H, J=8.2 Hz) and 3.79 (s, 6H); $^{13}$C NMR (CDCl$_3$): δ 191.7, 156.0, 148.5, 146.7, 140.9, 140.6, 137.4, 135.0, 131.7, 130.2, 127.6, 127.4, 127.3, 126.8, 126.7, 120.4, 114.7 and 55.4; HRMS (m/z): 485.1992 (M$^+$).

Synthesis of 5-(ditolylaminobiphenylene)thiophene-2-carbaldehyde (4T)

Compound 4T was synthesized in a procedure similar to that for 3T except that 4-bromobenzaldehyde was replaced by 5-bromothiophene-2-carbaldehyde in the same mole number, giving compound 4T as yellow solid in 72% yield.

The spectroscopic data of compound 4T were as follows: $^1$H NMR (CDCl$_3$): δ 9.89 (s, 1H), 7.74 (d, 1H, J=4.0 Hz), 7.71 (d, 2H, J=8.2 Hz), 7.62 (d, 2H, J=8.2 Hz), 7.41 (d, 1H, J=4.0 Hz), 7.05-7.08 (m, 10H) and 2.33 (s, 6H); $^{13}$C NMR (CDCl$_3$): δ 182.6, 154.1, 148.1, 144.9, 142.1, 141.7, 137.4, 132.9, 132.3, 131.1, 129.9, 127.3, 126.9, 126.7, 124.8, 123.7, 122.1 and 20.7; HRMS (m/z): 459.1646 (M$^+$) (calculated value: 459.1657).

Synthesis of 5-(dimethoxyphenylaminobiphenylene)thiophene-2-carbaldehyde (4M)

Compound 4M was synthesized in a procedure similar to that for 4T except that compound 2T was replaced by 2M in the same mole number, giving yellow solid of compound 4M in 68% yield.

The spectroscopic data of 4M were as follows: $^1$H NMR (CDCl$_3$): δ 9.89 (s, 1H), 7.74 (d, 1H, J=4.0 Hz), 7.71 (d, 2H, J=8.2 Hz), 7.62 (d, 2H, J=8.2 Hz), 7.41 (d, 1H, J=4.0 Hz), 7.05-7.08 (m, 10H) and 3.81 (s, 6H); $^{13}$C NMR (CDCl$_3$): δ 182.6, 154.1, 148.1, 144.9, 142.1, 141.7, 137.4, 132.9, 132.3, 131.1, 129.9, 127.3, 126.9, 126.7, 124.8, 123.7, 122.1 and 57.4; HRMS (m/z): 491.1551 (M$^+$) (calculated value: 491.1555).

Synthesis of p-bromo-N,N-ditolylaniline (5T)

Compound 5T was synthesized in a procedure similar to that for 2T except that 4,4'-dibromobiphenyl was replaced by 1,4-dibromobenzene in the same mole number, giving compound 5T as white solid in 72% yield.

The spectroscopic data of 5T were as follows: $^1$H NMR (CDCl$_3$): δ 7.27 (d, 2H, J=8.9 Hz), 7.06 (d, 4H, J=8.4 Hz), 6.97 (d, 4H, J=8.4 Hz), 6.89 (d, 2H, J=8.8 Hz) and 2.31 (s, 6H); $^{13}$C NMR (CDCl$_3$): δ 147.4, 144.9, 132.8, 131.8, 129.9, 124.6, 123.8, 113.5 and 20.8; HRMS (m/z): 351.0631 (M$^+$) (calculated value: 351.0623).

Synthesis of p-bromo-N,N-dimethoxyphenylaniline (5M)

Compound 5M was synthesized in a procedure similar to that for 5T except that di-p-tolylamine was replaced by di(p- methoxyphenyl)amine in the same mole ratio, giving compound 5M as white solid in 70% yield.

The spectroscopic data of 5M were as follows: $^1$H NMR (CDCl$_3$): δ 7.23 (d, 2H, J=8.9 Hz), 7.03 (d, 4H, J=8.9 Hz), 6.82 (d, 2H, J=8.9 Hz), 6.78 (d, 2H, J=8.9 Hz) and 3.79 (s, 6H); $^{13}$C NMR (CDCl$_3$): δ 156.0, 147.8, 140.5, 131.7, 126.5, 121.9, 114.7, 112.3 and 55.4; HRMS (m/z): 383.0512 (M$^+$) (calculated value: 383.0512).

Synthesis of N,N-ditolyl-p-(2'-thiophenyl)aniline (6T)

To a three-necked flask containing a mixture of 5T (2.2 g=6.19 mmol), PdCl$_2$(PPh$_3$)$_2$ (0.13 g=0.18 mmol) and 2-tributylstannylthiophene (5.3 mL=14.2 mmol) was added DMF (20 mL). The reaction mixture was stirred at 90° C. for 24 hours. After cooling, the reaction was quenched by adding MeOH and KF$_{(aq)}$ (saturated 15 mL). The mixture was extracted by CH$_2$Cl$_2$ and the organic layer dried by anhydrous MgSO$_4$. Evaporation of the solvent gave a crude product, which was purified by silica gel with hexane as eluent to obtain the product as white solid in 83% yield (1.82 g=5.14 mmol).

The spectroscopic data of 6T were as follows: $^1$H NMR (CDCl$_3$): δ 7.44 (d, 2H, J=8.7 Hz), 7.20 (d, 2H, J=4.3 Hz), 7.01-7.09 (m, 1H) and 2.33 (s, 6H); $^{13}$C NMR (CDCl$_3$): δ 147.6, 145.0, 144.4, 132.6, 129.8, 127.8, 127.6, 126.5, 124.6, 123.6, 122.5, 121.9 and 20.7; HRMS (m/z): 355.1405 (M$^+$) (calculated value: 355.1395).

Synthesis of N,N-dimethoxyphenyl-p-(2'-thiophenyl)aniline (6M)

Compound 6M was synthesized in a procedure similar to that for 6T except that compound 5T was replaced by 5M in the same mole number, giving compound 6M as a white solid in 85% yield.

The spectroscopic data of 6M were as follows: $^1$H NMR (CDCl$_3$): δ 7.43 (d, 2H, J=8.6 Hz), 7.17-7.18 (m, 2H), 7.09 (d, 4H, J=8.9 Hz), 7.03 (d, 1H, J=3.6 Hz), 7.02 (d, 1H, J=3.6 Hz), 6.95 (d, 2H, J=8.6 Hz), 6.85 (d, 4H, J=8.9 Hz) and 3.81 (s, 6H); $^{13}$C NMR (CDCl$_3$): δ 155.9, 148.1, 144.6, 140.7, 128.9, 127.9, 126.6, 126.3, 123.5, 121.7, 120.6, 114.6 and 55.4; HRMS (m/z): 387.1283 (M$^+$) (calculated value: 387.1293).

Synthesis of p-(5-(p-(ditolylamino)phenyl)thiophen-2-yl)-benzaldehyde (7T)

To a three-necked flask containing a mixture of 6T (4.40 g=12.4 mmol) in dry THF was adding dropwise BuLi (16.1 mmol, 1.6 M in a hexane solution of 10 mL) at −78° C., then the solution was allowed to warm up gradually to 0° C. for about 30 minutes. The solution was cooled again to −78° C., and to it was added dropwise tri-n-butylchloro-stannane (5.3 mL=16.1 mmol). The reaction was then warmed up to room temperature and stirred overnight. The reaction was quenched by adding water and extracted by CH$_2$Cl$_2$. The combined organic solution was dried by anhydrous MgSO$_4$ and then dried in vacuo to produce a crude product.

The crude product was dissolved in dry DMF, to which were added p-bromo-benzaldehyde (2.28 g=12.38 mmol) and PdCl$_2$(PPh$_3$)$_2$ (237 mg=0.37 mmol). The solution was heated to 90° C. for 24 hours and then cooled. The reaction was quenched by adding MeOH and KF$_{(aq)}$ (saturated 15 mL). The mixture was extracted by CH$_2$Cl$_2$, while the organic layer was dried over anhydrous MgSO$_4$. Evaporation of the solvent gave a product, which was purified by a silica gel column eluted with CH$_2$Cl$_2$/hexane (1/1) to obtain compound 7T as yellow solid in 68% yield (3.87 g=8.43 mmol).

The spectroscopic data of 7T were as follows: $^1$H NMR (CDCl$_3$): δ 9.96 (s, 1H), 7.85 (d, 2H, J=8.0 Hz), 7.73 (d, 2H, J=8.0 Hz), 7.43 (d, 2H, J=8.1 Hz), 7.39 (dd, 1H, J=3.6, 0.9 Hz), 7.19 (dd, 1H, J=3.6, 0.9 Hz), 7.07 (d, 4H, J=8.1 Hz), 6.99-7.02 (m, 6H) and 2.31 (s, 6H); $^{13}$C NMR (CDCl$_3$): δ 191.3, 148.2, 146.2, 144.7, 140.3, 140.1, 134.7, 133.0, 130.4, 129.9, 126.5, 126.3, 126.0, 125.4, 124.9, 123.1, 121.9 and 20.8; HRMS (m/z): 459.1666 (M$^+$) (calculated value: 459.1657).

Synthesis of p-(5-(p-(dimethoxyphenylamino)phenyl)thiophen-2-yl)-benzaldehyde (7M)

Compound 7M was synthesized in a procedure similar to that for 7T except that compound 6T was replaced by 6M in the same mole ratio, giving compound 7M as white solid in 68% yield.

The spectroscopic data of 7M were as follows: $^1$H NMR (CDCl$_3$): 9.96 (s, 1H), 7.84 (d, 2H, J=7.7 Hz), 7.72 (d, 2H, J=7.7 Hz), 7.41 (d, 2H, J=8.0 Hz), 7.38 (d, 1H, J=3.9 Hz), 7.17 (d, 1H, J=2.5 Hz), 7.06 (d, 4H, J=8.0 Hz), 6.90 (d, 2H, J=8.0 Hz), 6.83 (d, 4H, J=8.1 Hz) and 3.78 (s, 6H); $^{13}$C NMR (CDCl$_3$): δ 191.3, 156.1, 148.7, 146.3, 140.3, 140.1, 140.0, 134.6, 130.4, 126.8, 126.3, 126.0, 125.6, 125.3, 122.8, 120.0, 114.7 and 55.4. HRMS (m/z): 491.1561 (M$^+$) (calculated value: 491.1555).

Synthesis of 5-(5'-(p-ditolylaminophenyl)thiophen-2'-yl)thiophene-2-carbaldehyde (8T)

Compound 8T was synthesized in a procedure similar to that for 7T except that 4-bromobenzaldehyde was replaced by 5-bromothiophene-2-carbaldehyde in the same mole number, giving compound 8T as yellow solid in 70% yield.

The spectroscopic data of 8T were as follows: $^1$H NMR (CDCl$_3$): δ 9.83 (s, 1H), 7.64 (d, 1H, J=3.9 Hz), 7.41 (d, 2H, J=8.7 Hz), 7.28 (d, 1H, J=3.8 Hz), 7.21 (d, 1H, J=3.9 Hz), 7.13 (d, 4H, J=3.8 Hz), 7.09 (d, 4H, J=8.3 Hz), 6.99-7.04 (m, 6H) and 2.33 (s, 6H); $^{13}$C NMR (CDCl$_3$): δ 182.3, 148.4, 147.5, 146.5, 144.6, 141.1, 137.4, 133.7, 133.1, 130.0, 127.2, 126.4, 126.0, 125.0, 123.6, 122.8, 121.7 and 20.8; HRMS (m/z): 465.1215 (M$^+$) (calculated value: 465.1221).

Synthesis of 5-(5'-(p-dimethoxyphenylaminophenyl) thiophen-2'-yl)-thiophene-2-carbaldehyde (8M)

Compound 8M was synthesized in a procedure similar to that for 8T except that compound 6T was replaced by 6M in the same mole number, giving compound 8M as yellow solid in 73% yield.

The spectroscopic data of 8M were as follows: $^1$H NMR (CDCl$_3$): δ 9.83 (s, 1H), 7.64 (d, 1H, J=4.0 Hz), 7.38 (d, 2H, J=8.8 Hz), 7.28 (d, 1H, J=3.9 Hz), 7.20 (d, 1H, J=3.9 Hz), 7.11 (d, 1H, J=3.9 Hz), 7.07 (d, 4H, J=8.9 Hz), 6.90 (d, 2H, J=8.7 Hz), 6.84 (d, 4H, J=8.9 Hz) and 3.80 (s, 6H); $^{13}$C NMR (CDCl$_3$): δ 182.3, 156.2, 148.9, 147.5, 146.6, 141.0, 140.2, 137.4, 133.4, 127.2, 126.8, 126.4, 126.4, 125.1, 123.5, 122.5, 119.9, 114.7 and 55.4; HRMS (m/z): 497.1113 (M$^+$) (calculated value: 497.1119).

Synthesis of 5-(5'-(5"-bromothiophen-2"-yl) thiophen-2'-yl)-2-ditolylaminothiophene (9T)

Compound 9T was synthesized in a procedure similar to that for 2T except that 4,4'-dibromobiphenyl was replaced by 2,5-bis(5'-bromothiophen-2'-yl)thiophene in the same mole number, giving compound 9T as yellow solid in 55% yield.

The spectroscopic data of 9T were as follows: $^1$H NMR (CDCl$_3$): δ 7.09 (s, 8H), 6.95 (dd, 1H, J=3.8, 0.6 Hz), 6.91 (d, 1H, J=3.8 Hz), 6.87 (d, 1H, J=3.8 Hz), 6.86 (d, 1H, J=3.8 Hz), 6.48 (d, 1H, J=3.8 Hz) and 2.33 (s, 6H); $^{13}$C NMR (CDCl$_3$): δ 152.1, 145.2, 138.8, 137.4, 133.9, 133.0, 130.6, 129.8, 128.8, 124.4, 123.3, 123.0, 122.8, 122.5, 118.7, 110.6 and 20.8; HRMS (m/z): 520.9951 (M$^+$) (calculated value: 520.9941).

Synthesis of 5-(5'-(5''-bromothiophen-2''-yl) thiophen-2'-yl)-2-dimethoxyphenylamino-thiophene (9M)

Compound 9M was synthesized in a procedure similar to that for 9T except that di-p-tolylamine was replaced by di(p-methoxyphenyl)amine in the same mole ratio, giving compound 9M as yellow solid in 52% yield.

The spectroscopic data of 9M were as follows: $^1$H NMR (CDCl$_3$): δ 7.09 (s, 8H), 6.95 (dd, 1H, J=0.6, 3.8 Hz), 6.91 (d, 1H, J=3.8 Hz), 6.87 (d, 1H, J=3.8 Hz), 6.86 (d, 1H, J=3.8 Hz), 6.48 (d, 1H, J=3.8 Hz) and 3.80 (s, 6H); $^{13}$C NMR (CDCl$_3$): δ 152.1, 145.2, 138.8, 137.4, 133.9, 133.0, 130.6, 129.8, 128.8, 124.4, 123.3, 123.0, 122.8, 122.5, 118.7, 110.6 and 55.6; HRMS (m/z): 552.9854 (M$^+$) (calculated value: 552.9840).

Synthesis of 5-(5'-(5''-(ditolylamino)thiophen-2''-yl) thiophen-2'-yl)thiophene-2-carbaldehyde (10T)

To a three-necked flask containing a solution of compound 9T (0.90 g=1.73 mmol) in dry THF was added dropwise BuLi (2.6 mmol, 1.6 M in a hexane solution of 1.6 mL) at −78° C. The solution was allowed to warm up gradually to 0° C. for about 30 minutes. The solution was cooled again to −78° C., then to it was added dropwise DMF (0.2 mL=2.6 mmol). The reaction solution was warmed up to room temperature and stirred with a magnetic bar overnight. The reaction was quenched by adding distilled water and then extracted by CH$_2$Cl$_2$. The organic layers were combined and dried over anhydrous MgSO$_4$. The solvent was evaporated in vacuo to yield a crude product, which was purified by a silica gel column eluted with CH$_2$Cl$_2$/hexane (1/1) to obtain compound 10T as yellow solid in 40% yield (0.33 g=0.69 mmol).

The spectroscopic data of 10T were as follows: $^1$H NMR (CDCl$_3$): δ 9.82 (s, 1H), 7.62 (d, 1H, J=3.9 Hz), 7.19 (d, 1H, J=3.8 Hz), 7.15 (d, 1H, J=3.9 Hz), 7.05-7.09 (m, 8H), 6.94 (d, 1H, J=3.7 Hz), 6.90 (d, 1H, J=3.7 Hz), 6.44 (d, 1H, J=3.7 Hz) and 2.31 (s, 6H); $^{13}$C NMR (CDCl$_3$): δ 182.2, 153.1, 147.1, 145.6, 141.1, 140.1, 137.3, 133.4, 133.1, 129.8, 127.6, 126.9, 123.6, 123.3, 123.2, 123.0, 118.0 and 20.7; HRMS (m/z): 471.0793 (M$^+$) (calculated value: 471.0785).

Synthesis of 5-(5'-(5''-(dimethoxyphenylamino) thiophen-2''-yl)-thiophen-2'-yl)-thiophene-2-carbaldehyde (10M)

Compound 10M was synthesized in a procedure similar to that for 10T except that compound 9T was replaced by 9M in the same mole number, giving 10M as yellow solid in 60% yield.

The spectroscopic data of 10M were as follows: $^1$H NMR (CDCl$_3$): δ 9.80 (s, 1H), 7.60 (d, 1H, J=4.0 Hz), 7.17 (d, 1H, J=3.8 Hz), 7.12-7.14 (m, 5H), 6.90 (d, 1H, J=4.0 Hz), 6.83-6.87 (m, 5H), 6.30 (d, 1H, J=3.8 Hz) and 3.79 (s, 6H); $^{13}$C NMR (CDCl$_3$): δ 182.2, 156.3, 154.4, 147.1, 141.0, 140.8, 140.2, 137.4, 132.7, 126.9, 125.7, 125.2, 123.6, 123.5, 122.6, 115.0, 114.6 and 55.4; HRMS (m/z): 503.0691 (M$^+$) (calculated value: 503.0684).

Synthesis of (E)-2-cyano-3-(ditolylaminotriphenylene)acrylic Acid (1T-PPP)

A mixture of compound 3T (231 mg=0.51 mmol), cyanoacetic acid (52 mg=0.61 mmol) and ammonium acetate (10 mg=0.13 mmol) in acetic acid was placed in a three-necked flask under N$_2$-atmosphere and stirred at 120° C. for 12 hours. After cooling, the reaction was quenched by adding water and then extracted by CH$_2$Cl$_2$. The organic layer was dried over anhydrous MgSO$_4$ and the solvent evaporated under vacuum. The products were purified by a silica gel column eluted with CH$_2$Cl$_2$/acetic acid (19/1). The orange solid was isolated in 70% yield (185 mg=0.36 mmol).

The spectroscopic data of 1T-PPP were as follows: $^1$H NMR (DMSO-d$_6$): δ 8.33 (s, 1H), 8.11 (d, 2H, J=8.5 Hz), 7.92 (d, 2H, J=8.5 Hz), 7.83 (d, 2H, J=8.5 Hz), 7.73 (d, 2H, J=8.5 Hz), 7.63 (d, 2H, J=6.8 Hz), 7.29 (t, 4H, J=7.0 Hz) and 7.00-7.06 (m, 8H); $^{13}$C NMR (DMSO-d$_6$): δ 163.7, 154.1, 147.4, 147.3, 144.2, 140.1, 137.2, 133.2, 131.8, 130.8, 130.0, 127.9, 127.8, 127.4, 124.7, 123.8, 123.4, 116.7 and 103.4; HRMS (m/z): 492.1830 (M$^+$); elementary analysis: C=82.87, H=4.93, N=5.65, O=6.55 (calculated values: C=82.91, H=4.91, N=5.69, O=6.50).

Synthesis of (E)-2-cyano-3-(5'-(ditolylaminobiphenylene)thiophen-2'-yl)acrylic Acid (1T-PPS)

Compound 1T-PPS was synthesized in a procedure similar to that for 1T-PPP except that compound 3T was replaced by 4T in the same mole number, being obtained as red solid in 71% yield.

The spectroscopic data of 1T-PPS were as follows: $^1$H NMR (DMSO-d$_6$): δ 8.42 (s, 1H), 7.94 (d, 1H, J=4.0 Hz), 7.75 (d, 2H, J=8.3 Hz), 7.71 (d, 1H, J=4.0 Hz), 7.66 (d, 2H, J=8.3 Hz), 7.53 (d, 2H, J=8.6 Hz), 7.07 (d, 4H, J=8.2 Hz), 6.90 (d, 6H, J=8.3 Hz) and 2.23 (s, 6H); $^{13}$C NMR (DMSO-d$_6$): δ 164.1, 152.5, 148.0, 146.4, 144.7, 141.3, 140.9, 134.9, 133.0, 131.8, 130.9, 130.5, 127.7, 127.0, 127.0, 125.2, 125.0, 121.9, 117.1, 99.6 and 20.8; HRMS (m/z): 526.1710 (M$^+$).

Synthesis of (E)-2-cyano-3-(p-(5'-(p-ditolylamino) phenyl)thiophen-2'-yl)phenyl)-acrylic Acid (1T-PSP)

Compound 1T-PSP was synthesized in a procedure similar to that for 1T-PPP except that 3T was replaced by 7T in the same mole number, being obtained as black solid in 61% yield.

The spectroscopic data of 1T-PSP were as follows: $^1$H NMR (DMSO-d$_6$): δ 8.24 (s, 1H), 8.02 (d, 2H, J=8.4 Hz), 7.81 (d, 2H, J=8.4 Hz), 7.67 (d, 1H, J=3.8 Hz), 7.52 (d, 1H, J=8.6 Hz), 7.39 (d, 1H, J=3.8 Hz), 7.10 (d, 4H, J=8.4 Hz), 6.91 (d, 4H, J=8.32 Hz), 6.85 (d, 2H, J=8.6 Hz) and 2.23 (s, 6H); $^{13}$C NMR (DMSO-d$_6$): a 163.8, 153.5, 148.1, 145.4, 144.6, 140.0, 138.2, 133.3, 132.0, 130.5, 130.5, 127.7, 126.8, 126.3, 125.6, 125.1, 124.4, 121.6, 116.8, 103.2 and 20.8; HRMS (m/z): 526.1712 (M$^+$); elementary analysis: C=77.47, H=5.02, N=5.30, O=6.10, S=6.11 (calculated values: C=77.54, H=4.98, N=5.32, O=6.08, S=6.09).

Synthesis of (E)-2-cyano-3-(5'-(5''-(p-(ditolylamino) phenyl)thiophen-2''-yl)thiophen-2'-yl)acrylic Acid (1T-PSS)

Compound 1T-PSS was synthesized in a procedure similar to that for 1T-PPP except that 3T was replaced by 8T in the same mole number, being obtained as red solids in 68% yield.

The spectroscopic data of 1T-PSS were as follows: $^1$H NMR (DMSO-d$_6$): a 8.25 (s, 1H), 7.75 (d, 1H, J=3.7 Hz), 7.42-7.45 (m, 3H), 7.39 (d, 1H, J=3.7 Hz), 7.31 (d, 1H, J=3.7 Hz), 7.05 (d, 4H, J=8.1 Hz), 6.86 (d, 4H, J=8.0 Hz), 6.78 (d, 2H, J=8.2 Hz) and 2.20 (s, 6H); $^{13}$C NMR (DMSO-d$_6$): δ 164.8, 148.2, 145.5, 144.5, 139.8, 134.5, 133.4, 133.2, 130.5, 130.3, 128.1, 127.4, 126.7, 125.8, 125.2, 124.2, 121.4, 118.1, 102.9 and 20.8; HRMS (m/z): 532.1270 (M$^+$); elementary analysis: C=72.13, H=4.59, N=5.25, O=6.05, S=11.98 (calculated values: C=72.15, H=4.54, N=5.26, O=6.01, S=12.04).

Synthesis of (E)-2-cyano-3-(5'-(5''-(5'''-(ditolylamino)thiophen-2'''-yl)thiophen-2''-yl)-thiophen-2'-yl)acrylic Acid (1T-SSS)

Compound 1T-SSS was synthesized in a procedure similar to that for 1T-PPP except that 3T was replaced by 10T in the same mole number, being obtained as red solid in 57% yield.

The spectroscopic data of 1T-SSS were as follows: $^1$H NMR (DMSO-d$_6$): δ 8.28 (s, 1H), 7.77 (d, 1H, J=4.2 Hz), 7.39 (d, 1H, J=4.0 Hz), 7.37 (d, 1H, J=4.0 Hz), 7.07-7.10 (m, 6H), 6.95 (d, 4H, J=8.4 Hz), 6.38 (d, 1H, J=4.0 Hz) and 2.22 (s, 6H); $^{13}$C NMR (DMSO-d$_6$): δ 164.5, 152.8, 144.8, 144.7, 144.5, 140.2, 139.1, 134.5, 133.7, 132.8, 130.4, 128.0, 126.9, 124.9, 124.6, 124.2, 123.5, 118.0, 117.8, 101.2 and 20.7; HRMS (m/z): 538.0836 (M$^+$); elementary analysis: C=66.85, H=4.17, N=5.17, O=5.98, S=17.83 (calculated values: C=66.89, H=4.12, N=5.20, O=5.94, S=17.86).

Synthesis of (E)-2-cyano-3-(dimethoxyphenylamino-triphenylene)-acrylic Acid (1M-PPP)

Compound 1M-PPP was synthesized in a procedure similar to that of 1T-PPP except that 3T was replaced by 3M in the same mole number, being obtained as black solid in 64% yield.

The spectroscopic data of 1M-PPP were as follows: $^1$H NMR (DMSO-d$_6$): δ 8.14 (s, 1H), 7.99 (d, 2H, J=6.7 Hz), 7.82 (d, 2H, J=7.4 Hz), 7.74 (d, 2H, J=7.4 Hz), 7.65 (d, 2H, J=7.6 Hz), 7.50 (d, 2H, J=8.1 Hz), 6.99 (d, 4H, J=8.3 Hz), 6.87 (d, 4H, J=8.3 Hz), 6.78 (d, 2H, J=8.1 Hz) and 3.69 (s, 6H); $^{13}$C NMR (DMSO-d$_6$): δ 164.9, 156.3, 150.3, 148.5, 143.0, 140.2, 140.0, 137.0, 131.7, 131.0, 130.9, 127.6, 127.5, 127.2, 126.7, 119.7, 118.4, 115.4, 109.4 and 55.6; HRMS (m/z): 552.2048 (M$^+$).

Synthesis of (E)-2-cyano-3-(5'-(dimethoxyphenylaminobiphenylene)-thiophen-2'-yl)-acrylic Acid (1M-PPS)

Compound 1M-PPS was synthesized in a procedure similar to that for 1T-PPP except that 3T was replaced by 4M in the same mole number, being obtained as red solid in 76% yield.

The spectroscopic data of 1M-PPS were as follows: $^1$H NMR (DMSO-d$_6$): δ 8.46 (s, 1H), 7.98 (d, 1H, J=3.8 Hz), 7.78 (d, 2H, J=8.1 Hz), 7.75 (d, 1H, J=3.8 Hz), 7.68 (d, 2H, J=8.2 Hz), 7.54 (d, 2H, J=8.4 Hz), 7.03 (d, 4H, J=8.7 Hz), 6.90 (d, 4H, J=8.7 Hz), 6.80 (d, 2H, J=8.4 Hz) and 3.72 (s, 6H); $^{13}$C NMR (DMSO-d$_6$): δ 164.0, 156.3, 152.9, 148.8, 146.8, 141.7, 141.2, 140.1, 134.7, 130.7, 130.4, 127.6, 127.3, 127.1, 126.9, 125.3, 119.5, 116.9, 115.4, 98.8 and 55.6; HRMS (m/z): 558.1612 (M$^+$); elementary analysis: C=73.11, H=4.72, N=4.97, O=11.49, S=5.71 (calculated values: C=73.10, H=4.69, N=5.01, O=11.46, S=5.74).

Synthesis of (E)-2-cyano-3-(p-(5'-(p-di-methoxyphenylamino)-phenyl)-thiophen-2'-yl)phenyl)acrylic Acid (1M-PSP)

Compound 1M-PSP was synthesized in a procedure similar to that for 1T-PPP except that 3T was replaced by 7M in the same mole number, being obtained as red solid in 62% yield.

The spectroscopic data of 1M-PSP were as follows: $^1$H NMR (DMSO-d$_6$): δ 8.17 (s, 1H), 7.99 (d, 2H, J=8.4 Hz), 7.78 (d, 2H, J=8.4 Hz), 7.64 (d, 1H, J=3.8 Hz), 7.47 (d, 2H, J=8.6 Hz), 7.35 (d, 1H, J=3.8 Hz), 7.01 (d, 4H, J=8.9 Hz), 6.89 (d, 4H, J=8.9 Hz), 6.73 (d, 2H, J=8.6 Hz) and 3.70 (s, 6H); $^{13}$C NMR (DMSO-d$_6$): δ 164.2, 156.4, 152.1, 148.7, 145.5, 139.9, 139.7, 137.8, 131.6, 130.7, 127.4, 127.3, 126.6, 125.5, 125.0, 123.9, 119.3, 117.5, 115.4, 105.3 and 55.64; HRMS (m/z): 558.1605 (M$^+$); elementary analysis: C=73.06, H=4.70, N=4.97, O=11.51, S=5.76 (calculated values: C=73.10, H=4.69, N=5.01, O=11.46, S=5.74).

Synthesis of (E)-2-cyano-3-(5'-(5''-(p-(dimethoxyphenylamino) phenyl)thiophen-2''-yl)thiophen-2'-yl)acrylic Acid (1M-PSS)

Compound 1M-PSS was synthesized in a procedure similar to that of 1T-PPP except that 3T was replaced by 8M in the same mole number, being obtained as red solid in 76% yield.

The spectroscopic data of 1M-PSS were as follows: $^1$H NMR (DMSO-d$_6$): δ 8.32 (s, 1H), 7.81 (d, 1H, J=3.3 Hz), 7.43-7.46 (m, 4H), 7.31 (d, 1H, J=3.1 Hz), 7.00 (d, 4H, J=8.4 Hz), 6.89 (d, 4H, J=8.5 Hz), 6.69 (d, 2H, J=8.2 Hz) and 3.70 (s, 6H); $^{13}$C NMR (DMSO-d$_6$): δ 164.3, 156.5, 149.0, 146.1, 145.4, 145.3, 140.8, 139.8, 134.1, 132.9, 128.4, 127.5, 126.7, 124.7, 124.4, 123.9, 119.0, 117.6, 115.4 and 55.6; HRMS (m/z): 564.1181 (M$^+$); elementary analysis: C=68.02, H=4.31, N=4.92, O=11.38, S=11.37 (calculated values: C=68.06, H=4.28, N=4.96, O=11.33, S=11.36).

Synthesis of (E)-2-cyano-3-(5'-(5''-(5'''-(dimethoxyphenylamino)-thiophen-2'''-yl)-thiophen-2''-yl)thiophen-2'-yl)acrylic Acid (1M-SSS)

Compound 1M-SSS was synthesized in a procedure similar to that for 1T-PPP except that 3T was replaced by 10M in the same mole number, being obtained as black solid in 61% yield.

The spectroscopic data of 1M-SSS were as follows: $^1$H NMR (DMSO-d$_6$): δ 8.38 (s, 1H), 7.87 (d, 1H, J=4.0 Hz), 7.44 (d, 1H, J=4.0 Hz), 7.43 (d, 1H, J=4.0 Hz), 7.06-7.11 (m, 6H), 6.90 (dd, 4H, J=6.9, 2.1 Hz), 6.20 (d, 1H, J=4.0 Hz) and 3.72 (s, 6H); $^{13}$C NMR (DMSO-d$_6$): δ 164.1, 156.7, 154.8, 145.9, 145.5, 141.4, 140.4, 139.8, 134.0, 132.1, 128.4, 125.7, 125.4, 125.0, 124.8, 124.4, 123.7, 117.3, 115.3, 114.0, 99.8 and 55.7; HRMS (m/z): 570.0739 (M$^+$); elementary analysis: C=63.10, H=3.92, N=4.87, O=11.25, S=16.86 (calculated values: C=63.14, H=3.89, N=4.91, O=11.21, S=16.86).

Properties of the Compounds

The absorption spectra recording, redox potential measurements and quantum chemistry computations for the 1T-series and 1M-series compounds synthesized as above were made as in Example 1.

Figure 7:
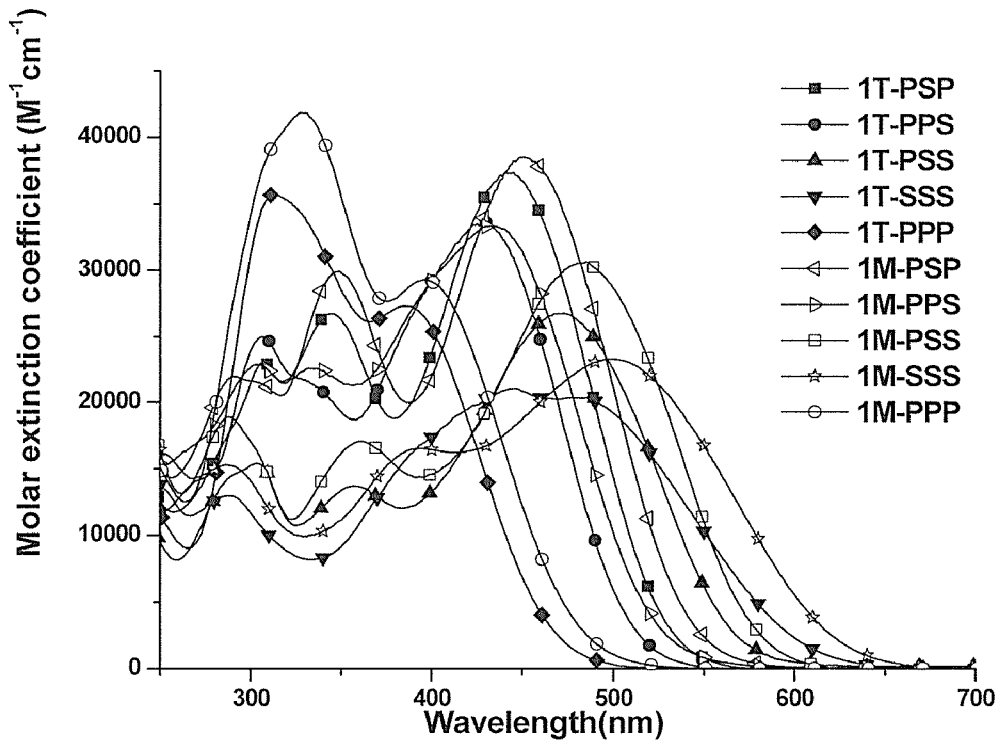
FIG. 7 shows the absorption spectra (in THF) of the dye compounds obtained in Example 2 of this invention, where "ε" is the molar extinction coefficient.
Figure 8:
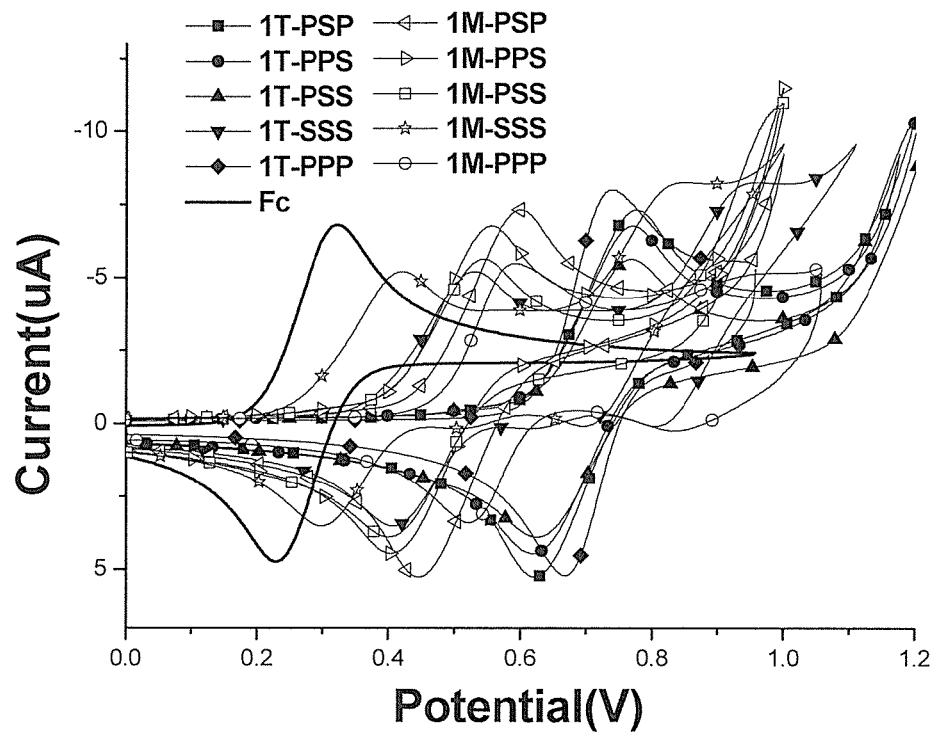
FIG. 8 shows the oxidative voltammograms of the dye compounds in Example 2.
Figure 9:
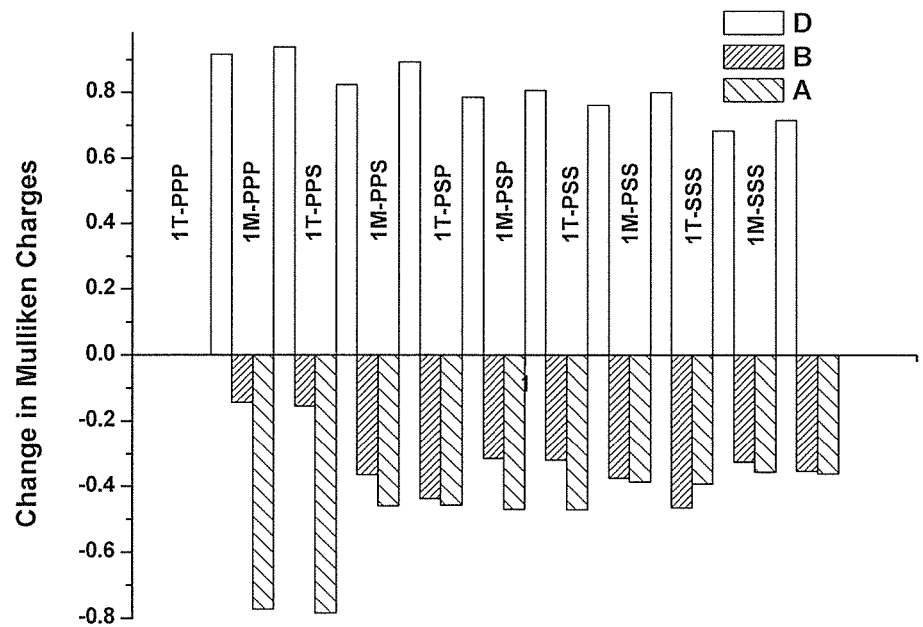
FIG. 9 shows the difference of Mulliken charges between the ground state ($S_0$) and the excited state ($S_1$) of the dye compounds in Example 2, which was estimated by the time dependent DFT/B3LYP model (ESI).
Figure 10:
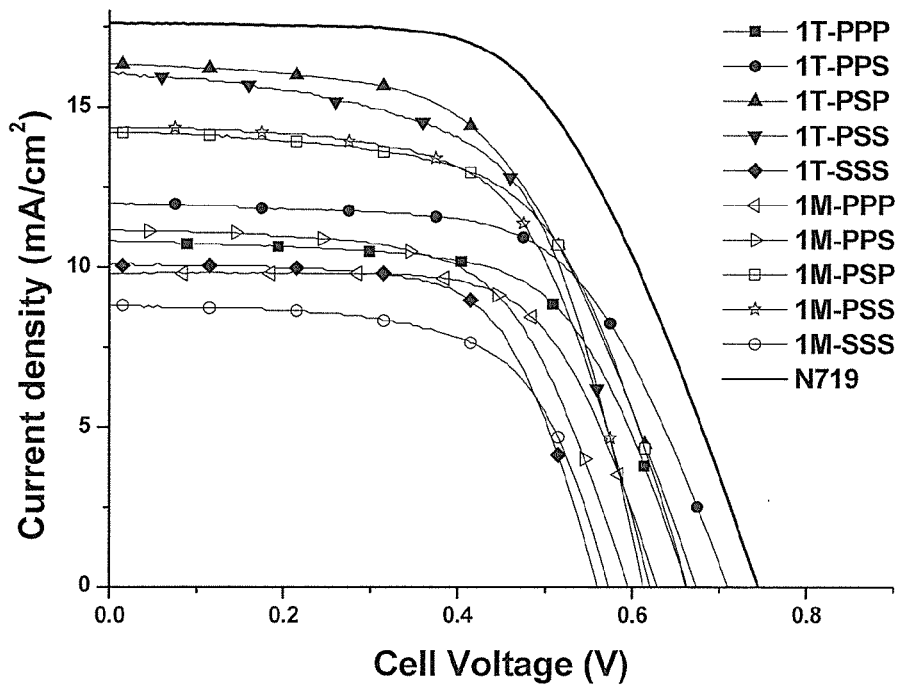
FIG. 10 shows the I-V curves of the compounds of the 1T-series and 1M-series in Example 2.
Figure 11:
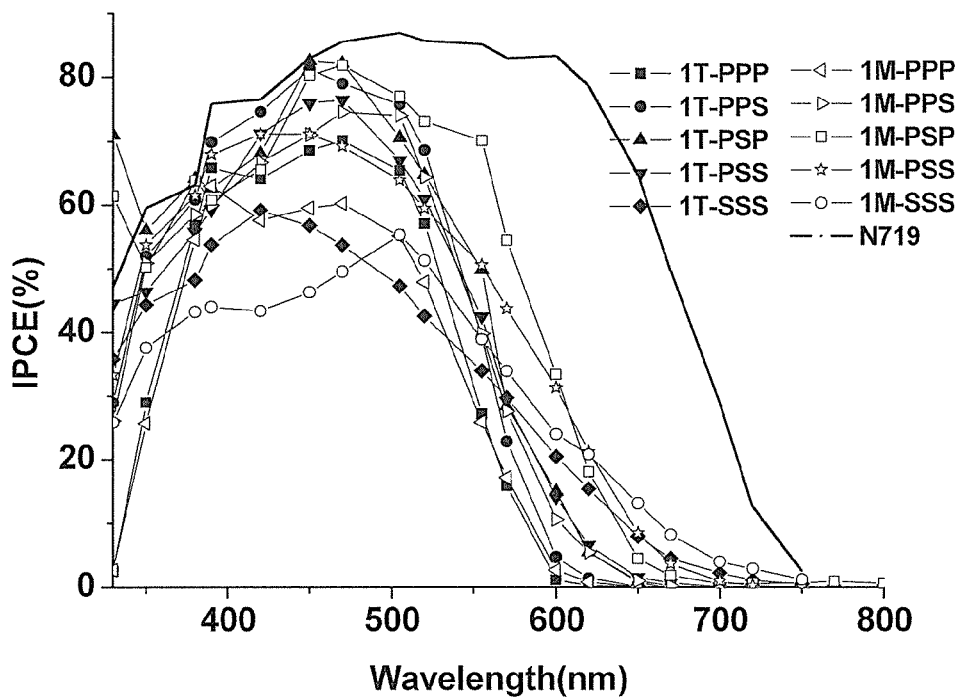
FIG. 11 is the IPCE plots of the compounds of the 1T-series and 1M-series in Example 2.

Specifically, FIG. 7 shows the absorption spectra (in THF) of the dye compounds obtained in Example 2 of this invention, where "ε" is the molar extinction coefficient. FIG. 8 shows the oxidative voltammograms of the dye compounds in Example 2. FIG. 9 shows the difference of Mulliken charges between the ground state ($S_0$) and the excited state ($S_1$) of the dye compounds in Example 2, which was estimated by the time dependent DFT/B3LYP model (ESI). FIG. 10 shows the I-V curves of the compounds of the 1T-series and 1M-series in Example 2. FIG. 11 is the IPCE plots of the compounds of the 1T-series and 1M-series in Example 2. The values of some property parameters are listed in Table 2.

Performances of the Compounds as Dye Sensitizers

The 1T-series and 1M-series compounds were further used to fabricate DSSCs in the same manner described in Example 1, and the performances of the DSSCs were measured in the same way. The performance parameters are also listed in Table 2.

This invention has been disclosed above in the preferred embodiments, but is not limited to those. It is known to persons skilled in the art that some modifications and innovations may be made without departing from the spirit and scope of this invention. Hence, the scope of this invention should be defined by the following claims.

and $B^1$ and $B^2$ each independently represent a substituted or unsubstituted aryl group.

2. The dye compound of claim 1, wherein $B^1$ and $B^2$ are each independently a phenyl group or a naphthyl group, in which arbitrary hydrogen atom may be substituted by a $C_1$-$C_3$ alkyl group or a $C_1$-$C_3$ alkoxy group.

3. The dye compound of claim 2, which is one of the following compounds

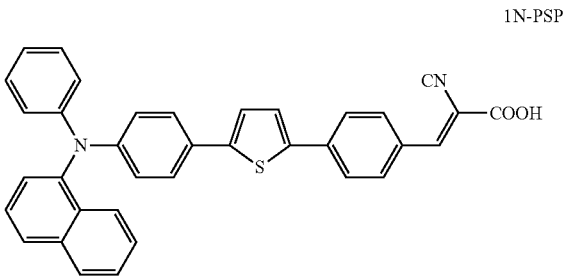

1N-PSP

TABLE 2

Calculated (TDDFT/B3LYP) and experimental parameters for the 1T-series and 1M-series dye compounds.

| Dye | HOMO/LUMO[a] (eV) | Band gap[a] | f[a] | $\lambda_{abs}$[b] (nm)/ (ε ($M^{-1}$ $cm^{-1}$)) | $E_{0-0}$[b] (eV) | $E_{ox}$[c] (V) | $E_{HOMO}/E_{LUMO}$[d] (V) | $J_{sc}$ (mA·$cm^{-2}$) | $V_{oc}$ (V) | FF | η[e] (%) |
|---|---|---|---|---|---|---|---|---|---|---|---|
| 1T-PPP | −4.96/−2.56 | 2.39 | 0.27 | 387 (27600) | 2.70 | 0.73 | 5.23/2.53 | 10.84 | 0.66 | 0.63 | 4.56 |
| 1T-PPS | −4.97/−2.63 | 2.34 | 0.38 | 430 (33700) | 2.51 | 0.72 | 5.22/2.71 | 12.00 | 0.71 | 0.61 | 5.26 |
| 1T-PSP | −4.96/−2.59 | 2.37 | 0.68 | 445 (37400) | 2.46 | 0.72 | 5.22/2.76 | 16.34 | 0.68 | 0.55 | 6.05 |
| 1T-PSS | −4.98/−2.65 | 2.32 | 0.83 | 473 (26800) | 2.31 | 0.71 | 5.22/2.91 | 16.08 | 0.60 | 0.59 | 5.70 |
| 1T-SSS | −4.90/−2.67 | 2.23 | 0.97 | 485 (20400) | 2.20 | 0.49 | 4.99/2.79 | 10.04 | 0.56 | 0.65 | 3.72 |
| 1M-PPP | −4.87/−2.52 | 2.26 | 0.24 | 399 (29700) | 2.64 | 0.42 | 4.92/2.77 | 9.8 | 0.63 | 0.66 | 4.14 |
| 1M-PPS | −4.79/−2.59 | 2.20 | 0.37 | 432 (33400) | 2.44 | 0.54 | 5.04/2.60 | 11.16 | 0.60 | 0.61 | 4.09 |
| 1M-PSP | −4.78/−2.55 | 2.23 | 0.62 | 451 (38600) | 2.38 | 0.59 | 5.09/2.71 | 16.60 | 0.65 | 0.56 | 5.98 |
| 1M-PSS | −4.83/−2.61 | 2.22 | 0.74 | 485 (30700) | 2.27 | 0.53 | 5.03/2.76 | 14.36 | 0.58 | 0.61 | 5.48 |
| 1M-SSS | −4.77/−2.62 | 2.15 | 0.91 | 498 (23400) | 2.15 | 0.42 | 4.92/2.77 | 9.08 | 0.54 | 0.61 | 3.02 |
| N719 | — | — | — | — | — | — | — | 17.68 | 0.75 | 0.61 | 7.64 | f: Oscillator Strength for the lowest energy transition;
ε: absorption coefficient;
$E_{ox}$: oxidation potential;
$E_{0-0}$: 0-0 transition energy measured at the intersection of absorption and emission spectra;
$J_{sc}$: short-circuit photocurrent density;
$V_{oc}$: open-circuit photovoltage;
FF: fill factor;
η: total power conversion efficiency.
[a]TDDFT/B3LYP calculated values.
[b]in THF.
[c]Oxidation potential in THF ($10^{-3}$ M) containing 0.1 M (n-$C_4H_9$)$_4$$NPF_6$ with a scan rate 100 mV · $s^{-1}$.
[d]$E_{HOMO}$ was calculated by $E_{ox}$ + 4.5 V (vs. NHE), and $E_{LUMO}$ = $E_{HOMO}$ − $E_{0-0}$.
[e]Performance of DSSC measured in a 0.25 $cm^2$ working area on a FTO (15 Ω/square) substrate.

What is claimed is:

1. A dye compound, expressed by formula (I):

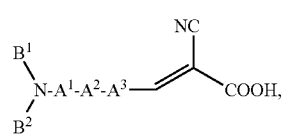

(I)

wherein $A^1$ and $A^3$ each independently represent a substituted or unsubstituted 1,4-phenylene group, $A^2$ represents a substituted or unsubstituted 2,5-thiophene group, -continued

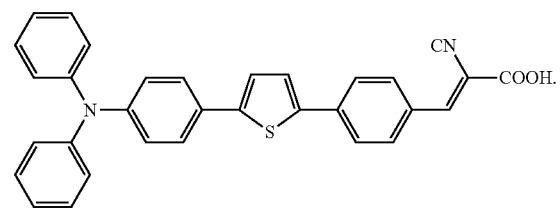

1P-PSP

4. The dye compound of claim 2, wherein the $C_1$-$C_3$ alkyl group is a methyl group.

5. The dye compound of claim 4, which is one of the following compounds
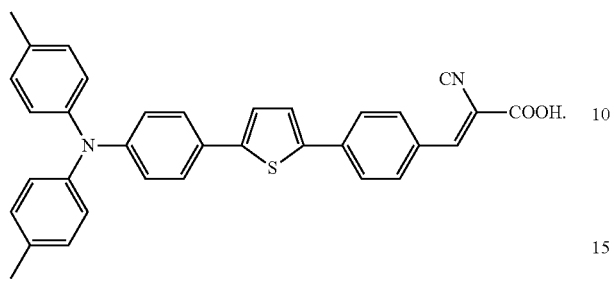
1T-PSP
6. The dye compound of claim 2, wherein the $C_1$-$C_3$ alkoxy group is a methoxy group.
7. The dye compound of claim 6, which is one of the following compounds
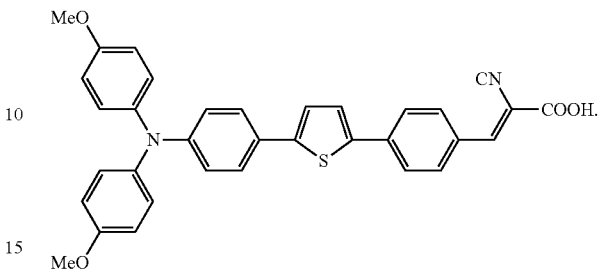
1M-PSP
* * * * *